United States Patent
Zur Hausen et al.

(10) Patent No.: US 10,457,938 B2
(45) Date of Patent: Oct. 29, 2019

(54) TTV MIRNA SEQUENCES AS AN EARLY MARKER FOR THE FUTURE DEVELOPMENT OF CANCER AND AS A TARGET FOR CANCER TREATMENT AND PREVENTION

(71) Applicant: DEUTSCHES KREBSFORSCHUNGSZENTRUM, Heidelberg (DE)

(72) Inventors: Harald Zur Hausen, Wald-Michelbach (DE); Ethel-Michel De Villiers, Wald-Michelbach (DE); Angel Cid-Arregui, Heidelberg (DE); Victor Sarachaga De Benito, Heidelberg (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 0 days.

(21) Appl. No.: 14/966,110

(22) Filed: Dec. 11, 2015

(65) Prior Publication Data

US 2016/0160216 A1 Jun. 9, 2016
US 2017/0283798 A9 Oct. 5, 2017

Related U.S. Application Data

(63) Continuation of application No. PCT/EP2014/078346, filed on Dec. 17, 2014, and a continuation-in-part of application No. PCT/EP2014/062251, filed on Jun. 12, 2014.

(30) Foreign Application Priority Data

Jun. 14, 2013 (EP) .................................... 13003062

(51) Int. Cl.
*C12N 15/11* (2006.01)
*C12N 15/113* (2010.01)
*C12Q 1/6886* (2018.01)

(52) U.S. Cl.
CPC ........ *C12N 15/113* (2013.01); *C12N 15/1131* (2013.01); *C12Q 1/6886* (2013.01); *C12N 2310/141* (2013.01); *C12N 2320/00* (2013.01); *C12N 2320/10* (2013.01); *C12Q 2600/178* (2013.01)

(58) Field of Classification Search
None
See application file for complete search history.

(56) References Cited

U.S. PATENT DOCUMENTS

| 5,702,891 | A | * | 12/1997 | Kolberg | ................. | C12Q 1/682 435/6.11 |
| 7,655,785 | B1 | * | 2/2010 | Bentwich | ............. | C12N 15/113 435/320.1 |
| 2003/0050470 | A1 | * | 3/2003 | An | ......................... | C07H 21/00 536/24.3 |
| 2005/0181439 | A1 | * | 8/2005 | Choi | .................... | C07K 14/315 435/6.15 |
| 2007/0044171 | A1 | * | 2/2007 | Kovalic | ............... | C07K 14/415 800/278 |
| 2009/0062131 | A1 | | 3/2009 | Mounts | | |
| 2009/0081675 | A1 | * | 3/2009 | Colston, Jr. | ............ | C12Q 1/689 435/6.18 |
| 2013/0267429 | A1 | * | 10/2013 | Gardner | .................. | G06F 19/20 506/8 |

FOREIGN PATENT DOCUMENTS

| EP | 1992691 A1 | 11/2008 | | |
| EP | 2399928 A1 | 12/2011 | | |
| WO | WO 0177384 A2 | * 10/2001 | ......... | C07K 14/4703 |
| WO | 2005/005658 A1 | 1/2005 | | |
| WO | WO-2011160848 A1 | * 12/2011 | ........... | C07K 14/005 |

OTHER PUBLICATIONS

Kincaid et al., "Virus-Encoded microRNAs: An Overview and a Look to the Future", PLOS Pathogens, Dec. 2012, vol. 8, No. 12, pp. 1-11.
De Villiers et al., "TTV Infection in Colorectal Cancer Tissues and Normal Mucosa", Int. J. Cancer, 2007, vol. 121,pp. 2109-2112.
McLaughlin-Drubin et al., "Viruses Associated with Human Cancer", Biochimica et Biophysica Acta, 2008, vol. 1782, pp. 127-150.
De Villiers et al., "The Diversity of Torque Teno Viruses: In Vitro Replication Leads to the Formation of Additional Replication-Competent Subviral Molecules", Journal of Virology, 2011, vol. 85, No. 14, pp. 7284-7295.
Liang et al, "A human Herpesvirus miRNA Attenuates Interferon Signaling and Contributes to Maintenance of Viral Latency by Targeting IKK", Cell Research, 2011, vol. 21, pp. 793-806.
Pfeffer et al, "Viruses, microRNAs and Cancer", Oncogene, 2006, vol. 25, pp. 6211-6219.
Kincaid et al, "A Human Torque Teno Virus Encodes a MicroRNA That Inhibits Interferon Signaling", PLOS Pathogens, 2013, vol. 9, No. 12, pp. 1-14.
Mitchell et al, "Circulating microRNAs as Stable Blood-Based Markers for Cancer Detection", PNAS, 2008, vol. 105, No. 30, pp. 10513-10518.

* cited by examiner

*Primary Examiner* — Ekaterina Poliakova-Georgantas
(74) *Attorney, Agent, or Firm* — Perkins Coie LLP; Viola T. Kung

(57) ABSTRACT

Described are TTV miRNAs and probes and primers comprising part of said TTV miRNA polynucleic acid. The use of said compounds for diagnosis of cancer or predisposition of cancer is also described.

3 Claims, 5 Drawing Sheets

Specification includes a Sequence Listing.

US 10,457,938 B2

TTV MIRNA SEQUENCES AS AN EARLY MARKER FOR THE FUTURE DEVELOPMENT OF CANCER AND AS A TARGET FOR CANCER TREATMENT AND PREVENTION

This application is a continuation of PCT/EP2014/078346, filed on Dec. 17, 2014; which claims the priority of PCT/EP2014/062251, filed on Jun. 12, 2014. This application is also a continuation-in-part of PCT/EP2014/062251, filed on Jun. 12, 2014, which claims the priority of EP 13003062.0, filed on Jun. 14, 2013. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Dec. 9, 2015, and a size of 32.9 kilobytes. The Sequence Listing filed via EFS-Web is part of the specification and is hereby incorporated in its entirety by reference herein.

TECHNICAL FIELD

The present invention relates to novel TTV miRNA as well as probes and primers comprising part of said novel TTV miRNA polynucleic acid. Finally, the present invention relates to the use of said compounds as an early marker for the future development of cancer.

BACKGROUND

Torque Teno Virus (TTV) is a viral species belonging to the family Anelloviridae, genus *Alphatorquevirus*. Viruses classified into this specie present a circular, single stranded DNA (ssDNA) genome of 3.7-3.8 Kb of length, and are non-enveloped [2,3]. They were first discovered in 1997 in a patient presenting post-transfusion non A to G hepatitis [1]. A high divergence in the nucleotide sequence among different TTV strains is observed, reaching to more than 70% in some cases. Although the genomic organization is also variable, all of them contain a non-coding region, spanning 1.2 Kb [22]. The non-coding region has been demonstrated to harbour a promoter in its 3' end [4] and a highly conserved region of 70 bp within this 3' end is hypothesized to be the origin of replication of the viruses. It is estimated that more than 90% of humans are infected with one or more TTV strains. The number of different isolates (more than 200), their ubiquity and the lack of reliable and simple techniques to differentiate between them, have made it difficult to obtain enough epidemiological evidence in support of a causative relationship between TTV infection and a specific disease [23-28]. TTV viruses are known to infect several human tissues [21]. Limited data are available on the replication cycle, and even less on the function of the proteins encoded by these viruses.

MicroRNAs (miRNA) are small RNA molecules ranging between 19 and 29 nt and usually of 22 nt in length. They mediate post-transcriptional gene silencing (PTGS) by inducing cleavage, destabilization or translational inhibition of a target messenger RNA (mRNA) [9,10,11,12]. They do that by guiding the RISC complex to a concrete mRNA, interacting with it by base pairing. This interaction is thought to be mediated mainly by a perfect match between the target mRNA 3' untranslated region (UTR) and the miRNA "seed" (nucleotides from 2 to 7) [7,8,80], whereas a perfect match means that each of the "seed" nucleotides hybridizes by a Watson and Crick pairing with respective nucleotides of the target mRNA. In contrast, recent findings suggest that non-perfect matches (no Watson and Crick pairing or seeds containing one mismatch) in this region are more abundant than perfect matches [6]. The same study suggests that miRNA-mRNA pairings in coding sequences (CDS) are as abundant as those in 3"UTRs. Moreover, they demonstrate that some miRNAs tend to hybridize with mRNAs in a region totally different from the seed, and they are still able to exert PTGS. To increase even more the complexity of the miRNA-based gene expression regulation, in the last few years some examples of transcriptional gene silencing (TGS) and transcriptional gene activation (known as RNA activation (RNAa)) mediated by miRNA have appeared [29-33]. While the mechanisms mediating these two events are still poorly understood, it cannot be discarded that TGS and RNAa are general features of some miRNA. The number of known endogenous human miRNAs has increased very fast in the last few years. The number of mature miRNA annotated in miRBase is 2042 [13-16]. In addition, a large number of virally encoded miRNA has also been shown to use the cellular miRNA silencing machinery. Since the discovery of the first human viral encoded miRNA [5] its number has increased to 157 [13-16]. The majority of these miRNA are encoded by DNA viruses, especially those belonging to Herpesviridae and Polyomaviridae families. Recently, a bovine oncogenic RNA virus (Bovine Leukemia Virus) was reported to encode 8 mature miRNA, demonstrating that this type of viruses also can express them. Despite the large number of viral miRNA discovered, the function of most of them still remains elusive, although in the last years some reports have shed light over this issue. For instance, miRNAs encoded by both Polyoma and Herpes viruses have been demonstrated to help these viruses to escape the host immune response, by regulating viral [17] or host [18,19] protein expression. Another important finding was made some months ago when it was demonstrated that Epstein-Barr virus-encoded miRNAs are sufficient to transform cells by themselves [20], suggesting that viral miRNAs could be able to mediate an oncogenic process under the adequate conditions. Very recently, it was shown that TTV encode for miRNA's, and the role of one of this miRNA's in interferon signalling inhibition was demonstrated [78]

APC (*Adenomatous Polyposis coli*) is a very important tumour suppressor, especially in the context of colorectal cancer. Virtually all colorectal cancers carry inactivating APC mutations or epigenetic changes inactivating the transcription of this gene. Its tumour suppressor activity is thought to be mediated by its function in inhibition of wnt signalling, although it has also been implicated in migration and correct mitotic spindle assembly.

SUMMARY OF THE INVENTION

The technical problem underlying the present invention is to provide means (or markers) for diagnosis of cancer or diagnosis of a disposition to said disease. Another technical problem is to provide means for preventing cancer development and cancer recurrence by inhibiting a specific target.

The solution to said technical problem is achieved by providing the embodiments characterized in the claims.

Few aspects are known concerning the interaction between TTVs and their host. In the studies resulting in the present invention it was elucidated that TTV encode miRNAs, as well as their significance for the TTV infection and pathogenicity, mainly focusing on their possible role in cancer. Pre-miRNAs expressed by TTV strains are provided. The miRNA are transcribed from the non-coding region of the virus, in both sense and antisense orientations. Some miRNAs encoded in both orientations can, directly or indirectly, downregulate the tumor suppressor *Adenomatous Polyposis Coli* (APC) at the mRNA level. Surprisingly, the inventors identified a link between TTV and tumour suppressor regulation and this finding suggests a role of TTV in cancer development. This work represents the first molecular link between TTV and cancer.

(B-E) Northern blots showing the results with the indicated probes and transfections (Sense—HEK293TT cells transfected with pCDNA3.1(+)-TTV-HD14a-NCR-Sense. Anti-sense—HEK293TT cells transfected with pCDNA3.1(+)-TTV-HD14a-NCR-AntiSense. Mock—HEK293TT cells transfected with pCDNA3.1(+)). Probe sequences are listed in Table 4.

Figure 3:
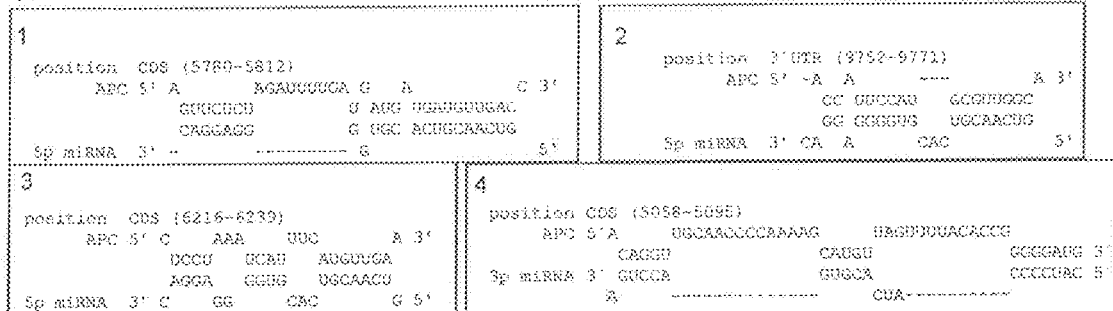
Figure 3:
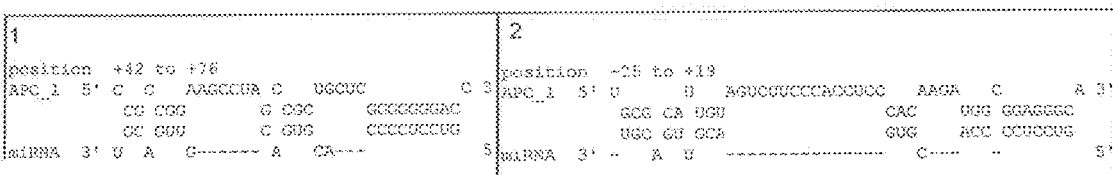
Figure 3:
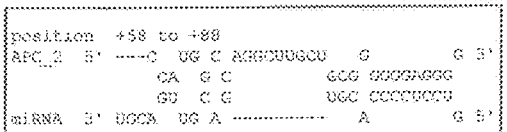
Figure 3:
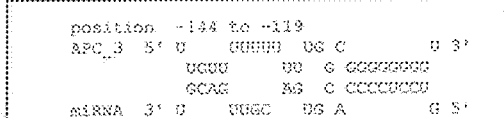
Figure 3:
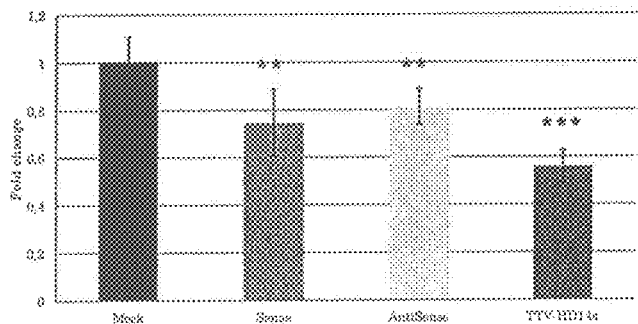

FIG. 3: Complementarity of TTV-HD14a-mir-2-5p with APC mRNA and TTV-HD14a-ASmir-8-3p with the APC promoters and APC mRNA down-regulation in transfected cells (A) Complementarity between TTV-HD14a-mir-2, p (1 (SEQ ID NO:77), 2 (SEQ ID NO:82) and 3 (SEQ ID NO:84)) TTV-HD14a-mir-2-3p(4 (SEQ ID NO:86)) with respective APC mRNA (SEQ ID NOs: 76,81, 83 and 85). Positions relative to APC transcript variant 2 (NCBI accession number: NM_001127510.2; SEQ ID NO:82).

(B, C and D) Complementarity between TTV-HD14a-ASmir-2-3p (B1: (SEQ ID NO:88, B2: (SEQ ID NO:90), C: (SEQ ID NO: 92), D: (SEQ ID NO: 94) and respectively APC promoters 1 (B1: (SEQ ID NO:87), B2 (SEQ ID NO:89), 2 (C: (SEQ ID NO: 91) and 3 (D: (SEQ ID NO: 93), respectively, as stored in EPDNew Human. The shown positions relate to the transcription start site (TSS) in reference to EPD New Human (EPDNew Human names: APC_1, APC_2 and APC_3).

(E) Relative expression levels of APC as measured by qPCR (Mean for Sense=0.747 and for AntiSense=0.650). ΔCt was calculated respect to HPRT. ΔΔCt was calculated respect to mock transfected cells. Differential values were normalized to 1. Sense—Relative values for HER 293TT cells transfected with pCDNA3.1(+)-TTVHD14a-NCR-Sense. Antisense—Relative values for HEK293TT cells transfected with pCDNA3.1(+)-TTVHD14a-NCR-Anti-Sense. Mock—Relative values for HEK293TT cells transfected with pCDNA3.1(+). TTV-HD14a—Relative values for cells transfected with the full-length TV-HD14a virus. +−SD; N=6. Statistical significance calculated using unpaired two-tailed Student T-Test.

Figure 4:
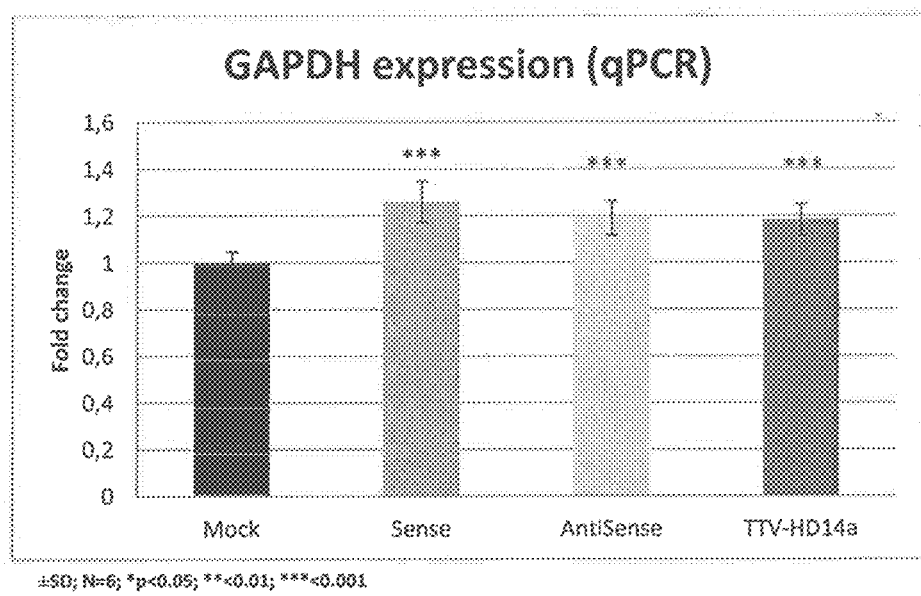

FIG. 4: GAPDH expression (see Example 6 for details) Relative expression levels of GAPDH as measured by gPCR. ΔCt was calculated. respect to HPRT. ΔΔCt was calculated respect to mock transferred cells. Differential values were normalized to 1. Sense Relative values for HER 293TT cells transfected with pCDNA3.1(+)-TTVHD14a-NCR-Sense. Antisense—Relative values for HEK293TT cells transfected with pCDNA3.1(+)-TTVHD14a-NCR-AntiSense. Mock—Relative values for HEK293TT cells transfected with pCDNA3.1(+). TTV-HD14a—Relative values for cells transfected with the full-length TTV-HD14a virus. +−SD; N=6, Statistical significance calculated using unpaired two-tailed Student T-Test.

Figure 5:
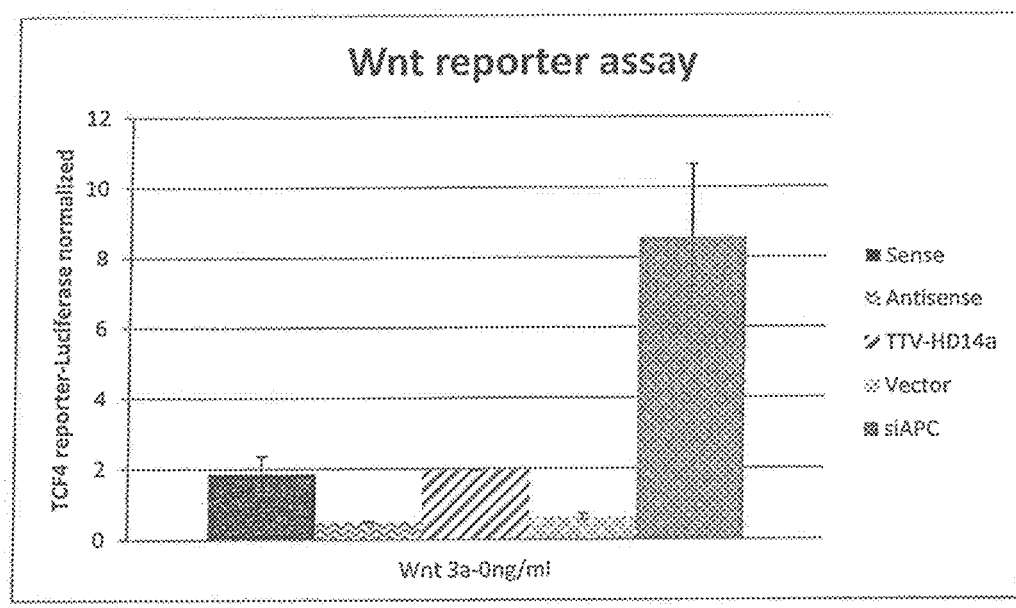
Figure 5:
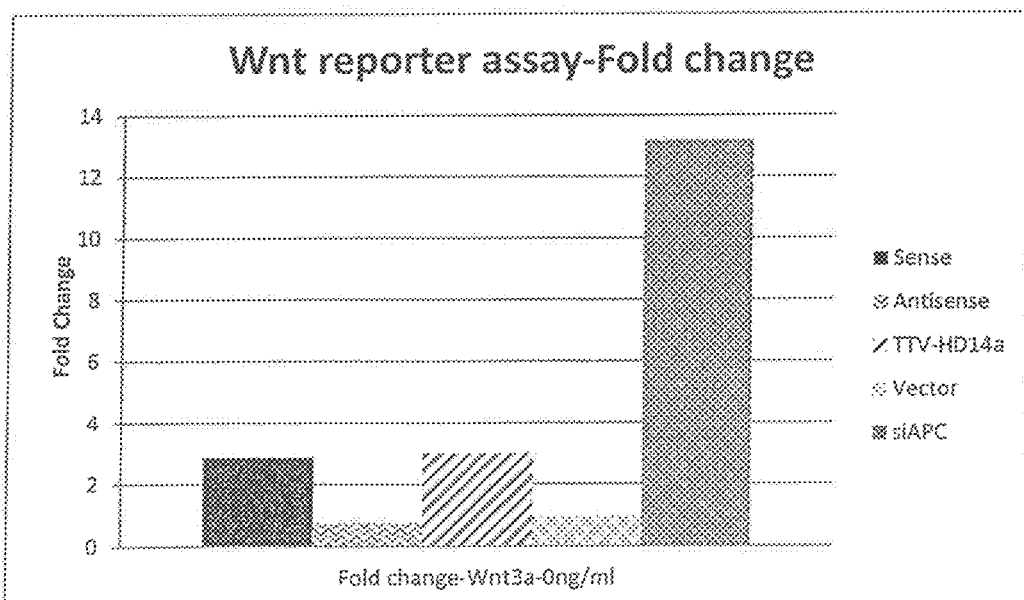

FIG. 5: Wnt upregulation by TTV-HD14a miRNA's HEK293TT were transfected in a 24 well format with 300 ng of TTV-HD14a virus or pCDNA-3.1(−)-TTV-HD14a-NCR(2820-3516) Sense (referred in the graphic as "Sense") or pCDNA-3.1(−)-TTV-HD14a-NCR(3516-2820)-Anti-Sense (referred in the graphic as "Antisense") or pCDNA3.1 (−) (referred in the graphic as "Vector") or Silencer siAPC (Life technologies) plus 60 ng of TOPFLASH vector (provided by *M. Boutros* lab) and 5 ng of CMV-*renilla*. Luciferase activity was measured 72 h after transfection. (A) *Firefly luciferase* units normalized to *Renilla luciferase* (B) Fold change respect to vector.

Accordingly, the present invention relates to a TTV polynucleic acid comprising: (a) a nucleotide sequence depicted in Table 1, 2a or 2b; (b) a nucleotide sequence having at least 60% identity to the nucleotide sequence of (a) and containing the nucleotide sequence CATCCYY (with Y=C or T); (c) a fragment of the nucleotide sequence of (a) or (b) and containing the nucleotide sequence CATCCYY (with Y=C or T); or (d) a nucleotide sequence which is complementary to any of said nucleotide sequences.

A further embodiment of the present invention relates to a TTV polynucleic acid, wherein the TTV polynucleic acid is a mature TTV miRNA molecule consisting of 19 to 29 nt, preferably about 22 nt, and comprise the nucleotide sequence CATCCY (with Y=C or T) or CAUCCYY (with Y: C or U). In a preferred embodiment the mature TTV miRNA molecule according to the invention (a) is a nucleotide sequence underlined in Table 2a or 2b; (b) consists of a nucleotide sequence having at least 60%, preferably at least 80%, most preferably at least 90% identity to the nucleotide sequence of (a) underlined in Table 2A or 2B and comprises the nucleotide sequence CATCCYY (with Y=C or T) or CAUCCYY (with Y: C or U); (c) is a fragment of a nucleotide sequence of (a) underlined in Table 2A or 2B and comprises the nucleotide sequence CATCCYY (with Y=C or T) or CAUCCYY (with Y: C or U) or (d) is a nucleotide sequence being complementary to a nucleotide sequence of (a), (b) or (c). In the context of the present invention a "mature TTV miRNA" is a polynucleic acid of an miRNA derived from a TTV.

The term "polynucleic acid" refers to a single-stranded or double-stranded nucleic acid sequence. A polynucleic acid may consist of deoxyribonucleotides or ribonucleotides, nucleotide analogues or modified nucleotides or may have been adapted for diagnostic or therapeutic purposes. A polynucleic acid may also comprise a double stranded cDNA clone which can be used, for example, for cloning purposes. In the following statements and findings made on the DNA level apply to the RNA level accordingly and vice versa.

The TTV polynucleic acid and the mature TTV miRNA of the invention can be prepared according to well-known routine methods, for example, by (a) isolating the entire DNA or, preferably, RNA from a sample, (b) detecting the TTV sequence by hybridization or PCR and (c) cloning of the TTV sequence into a vector (d) by synthesis of the respective nucleotides of the miRNA sequence.

Also included within the present invention are sequence variants of the polynucleic acid and the mature TTV miRNA molecules of the invention containing either deletions and/or insertions of one or more nucleotides, especially insertions or deletions of one or more codons, mainly at the extremities of oligonucleotides (either 3' or 5') and which show at least 60%, 70%, 80%, 90%, 95% or 98% identity to said polynucleic acid sequence of the invention and contain the consensus sequence CATCCYY (with Y=C or T). Polynucleic acid sequences according to the present invention which are similar to the sequence as shown in Table 1, 2a or 2b can be characterized and isolated according to any of the techniques known in the art, such as amplification by means of sequence-specific primers, hybridization with sequence-specific probes under more or less stringent conditions, sequence determination of the genetic information of TTV etc. The variants and fragments of the TTV polynucleic acid sequences of the present invention are still able to interfere with or inhibit the expression of their target gene, for example APC.

In a particular preferred embodiment the TTV polynucleic acid sequence (if DNA) contains the consensus sequence CATCCYY (with Y=C or T), i.e. CATCCCC, CATCCCT, CATCCTC or CATCCTT. In another particular preferred embodiment the TTV polynucleic acid sequence (if RNA) contains the consensus sequence CAUCCYY (with Y=C or U), i.e. CAUCCCC, CAUCCCU, CAUCCUC or CAUCCUU. In this regard particular reference is made to Table 2b below.

In a particular preferred embodiment the inventors show how the most conserved seed motif (AUCCUC) has three additional possible interaction sites within APC mRNA in addition to the previously described for TTV-HD14a-mir-2-3p. In this regard particular reference is made to Table 8 below. Therefore, in a further embodiment the invention relates to variants of the polynucleic acid as described above which comprise the seed motif AUCCCUC and bind to at least one of the interaction sites within APC mRNA shown in Table 8 and, preferably, downregulate APC.

Also included in the present invention are analogous miRNAs in other human TT virus types and variants and in similarly structured single-stranded DNA viruses of the human or animal origin. Anelloviruses have been demonstrated in domestic animals in part with similar nucleotide sequences as human TT viruses [77].

Furthermore, the present invention relates to an oligonucleotide primer comprising part of the TTV polynucleic acid of the present invention, said primer being capable of acting as primer for specifically sequencing or specifically amplifying a certain TTV miRNA.

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow to specifically prime the synthesis of the extension products. Preferably the primer is at least about 10, preferably at least 15 nucleotides. Specific length and sequence will depend on the complexity of the required DNA or RNA targets, as well as on the conditions of primer use such as temperature, ionic strength etc. The amplification primers do not have to match exactly with the corresponding template sequence to warrant proper amplification. The amplification method used can be either polymerase chain reaction (PCR), ligase chain reaction (LCR), nucleic acid sequence-based amplification (NASBA), transcription-based amplification system (TAS), strand displacement amplification (SDA) or amplification by means of Qß replicase or any other suitable method to amplify nucleic acid molecules using primer extension. During amplification or synthesis, the amplified products can be conveniently labelled either using labelled primers or by incorporating labelled nucleotides. Labels may be isotopic ($^{32}$P, $^{35}$S, etc.) or non-isotopic (biotin, digoxigenin, etc.).

The present invention also relates to an oligonucleotide probe comprising part of the TTV polynucleic acid of the present invention, said probe being capable of acting as a hybridization probe for specific detection of a certain TTV miRNA in vitro and in vivo.

The term "probe" refers to single stranded sequence-specific oligonucleotides which have a sequence which is complementary to the target sequence of the TTV polynucleic acid to be detected. Preferably, these probes are about 5 to 50 nucleotides long, more preferably from about 10 to 25 nucleotides. The probe can be fixed to a solid support, i.e., any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, NH, groups, SH groups, carboxylic groups, or coupling with biotin or haptens.

In an embodiment of the invention the probe is an anti-miR oligonucleotide. An anti-miR oligonucleotide is a single-stranded RNA complementary to the miRNA molecule according to the invention. It can be delivered in its RNA form or being expressed from a vector, using a polymerase III promoter. Such an anti-miR oligonucleotide can be used for inhibiting the miRNA of the present invention. Methods for inhibiting miRNA by anti-miRs are described by Stenvang et al. in [81], which publication is incorporated by reference.

A further embodiment of the invention are miRNA sponges. A miRNA sponge is a messenger RNA with several, preferably 6-8, perfect complementary binding sites to the polynucleotide acid, i.e. mature TTV miRNA, of the invention. The binding sites can also include mismatches in the nucleotides from 10 to 13 of the mature TTV miRNA, to avoid direct RNA slicing and degradation which makes them more effective.

A further embodiment of the invention are tough decoy inhibitors. A tough decoy inhibitor is a miRNA consisting of a hairpin comprising a large internal bulge exposing two of the miRNA interaction sites of APC shown in Table 8 with imperfect baise-pairing with the TTV miRNA of the invention. The design of such a tough decoy inhibitor and methods of suppressing miRNA by a tough decoy inhibitor are described in [82] and [83] which are incorporated by reference.

The anti-miR, miRNA spounge and tough decoy inhibitor according to the invention are inhibitors of the TTV polynucleic acid as described above, in a preferred embodiment of a mature TTV miRNA shown underlined in Table 2A and 2B, which prevent the interaction between the TTV polynucleic acid and APC such that APC is not downregulated.

The present invention also relates to a vector containing a TTV polynucleic acid, oligonucleotide primer, oligonucleotide probe, anti-miR, miRNA sponge or tough decoy inhibitor of the invention allowing, e.g., expression, mutagenesis or a modification of a sequence by recombination of DNA sequences. Preferably, the vectors are plasmids, cosmids, viruses, bacteriophages and other vectors usually used in the field of genetic engineering. Vectors suitable for use in the present invention include, but are not limited to the T7-based expression vector for expression in mammalian cells and baculovirus-derived vectors for expression in insect cells. Preferably, the polynucleic acid of the invention or part thereof is operatively linked to the regulatory elements in the recombinant vector of the invention that guarantee the transcription and synthesis of an mRNA in prokaryotic and/or eukaryotic cells that can be translated. The nucleotide sequence to be transcribed can be operably linked to a promoter like a T7, metallothionein I or polyhedrin promoter.

The present invention also relates to recombinant host cells transiently or stably containing the TTV polynucleic acid (or fragments thereof) or vectors of the invention. A host cell is understood to be an organism that is capable to take up in vitro recombinant DNA and, if the case may be, to synthesize the polypeptids encoded by the polynucleotides of the invention. Preferably, these cells are prokaryotic or eukaryotic cells, for example mammalian cells, bacterial cells, insect cells or yeast cells.

The present invention also relates to a diagnostic kit containing a TTV polynucleic acid, an oligonucleotide primer, an oligonucleotide probe, a polypeptide and/or an antibody of the present invention.

For hybridization based assays, according to the hybridization solution (SSC, SSPE, etc.), the probes should be stringently hybridized to the target (with or without prior amplification) at their appropriate temperature in order to attain sufficient specificity. However, by slightly modifying the polynucleotide, (DNA and/or RNA) probes, either by adding or deleting one or a few nucleotides at their extremities (either 3' or 5'), or substituting some non-essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results.

Suitable assay methods for purposes of the present invention to detect hybrids formed between the oligonucleotide probes and a TTV polynucleic acid in a sample may comprise any of the assay formats known in the art, such as the conventional dot-blot format, sandwich hybridization or reverse hybridization. For example, the detection can be accomplished using a dot blot format, the unlabelled amplified sample being bound to a membrane, the membrane being incorporated with at least one labelled probe under suitable hybridization and wash conditions, and the presence of bound probe being monitored. An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

The present invention also relates to the use of a TTV polynucleic acid, an oligonucleotide primer, or an oligonucleotide probe of the present invention as an early marker for the future development of cancer, preferably colorectal or colon cancer.

Accordingly, an embodiment of the present invention relates to a method of detecting or diagnosing of colon cancer, comprising the steps of:
(a) isolating miRNA from a patients sample;
(b) sequencing the miRNA isolated in step (a); and
(c) determining, if an miRNA selected from the miRNA shown in Table 2B is present in the sample, whereas the presence of an miRNA shown in Table 2B indicates colon cancer.

For determining miRNA labelled oligonucleotides may be used.

Optionally, the method may comprise a further step (d) of quantifying the miRNA level in sample to distinguish between patients with colon cancer from healthy controls.

Preferably, in step (a) the miRNA is isolated from plasma or serum and the miRNA is quantified by using TaqMan miRNA qRT-PCR-assays as described in [86] which is incorporated by reference.

Alternatively, the miRNA may be isolated directly from the tumor and a miRNA sequencing may be performed to detect the miRNA or sections of any kind (e.g. cryo-sections, sections from paraffin embedded tissue) may be made directly on the tumor and an hybridization for the miRNA as described above may be performed in-situ.

Finally, the present invention also relates to the use of a TTV polynucleic acid of the present invention as a lead component for the development of a medicament for prevention or treatment of cancer, preferably colorectal or colon cancer. These medicaments may be inhibitors of any interaction between miRNAs and tumour suppressor genes to avoid cancer development or recurrence and cancer treatment. Thus, the specific TT virus miRNA or of its derivatives or of related miRNAs are useful for diagnostic, prevention or therapeutic applications in the cancer field.

Such inhibitor of an interaction between miRNA and tumor suppressor genes, for example APC, can be an anti-miR, A miRNA sponge or a tough decoy inhibitor as described above.

The inhibitor can be delivered to the tumor site by using an adeno associated virus (AAV) in order to deliver the inhibitor to counter effect the TTV miRNA according to the invention. An AAV gene therapy suitable for delivering one of the above miRNA inhibitors to the tumor is described in [84] which is incorporated by reference.

A further example of a suitable method for delivering the above inhibitors against TTV miRNA to a tumor is known as low pH-induced transmembrane structure (pHILP) [85]. This phILP construct consists of a peptide that crosses the plasma membrane only under acidic conditions which are typical of the tumor microenvironment. A peptide nucleic acid of an TTV miRNA inhibitor can be attached to this pHILP in order to be delivered specifically to cells in the tumor microenvironment. Preferably, this peptide is an anti-miR, which will cause the inhibition of the TTV miRNA according to the invention. A suitable method for delivering a TTV miRNA inhibitor with a pHILP construct is described in [85] which is incorporated by reference.

A further embodiment of the invention is a method of delivering a lead component for the development of a medicament for prevention or treatment of cancer, preferably colorectal cancer comprising the step of administrating to a patient suffering from a cancer, in particular colorectal cancer (a) a pharmaceutical composition comprising an adeno-associated virus expressing an inhibitor of the miRNA of the invention selected from the group consisting of anti-miR, miRNA sponge and tough decoy inhibitor of a miRNA interacting with a tumor suppressor gene and a pharmaceutically acceptable carrier or (b) a pharmaceutical composition comprising an inhibitor of the miRNA of the invention attached to a pHILP construct and a pharmaceutically acceptable carrier.

A further embodiment of the invention is (a) an adeno-associated virus for the use of delivering an inhibitor of TTV miRNA to tumor cells or (b) a pHILP construct for the use of delivering an inhibitor of a miRNA of the invention to tumor cells.

Preferably, the inhibitor to be delivered is selected from the group consisting of anti-miR, miRNA sponge and tough decoy inhibitor and is an inhibitor of a mature TTV miRNA as shown underlined in Table 2B which interacts with APC.

The following examples illustrate the invention and are not construed as any limitation of the invention.

EXAMPLE 1

Material and Methods (A) Cell Culture and Transfections

HEK293TT cells [76] cultured in Dulbeco's Eagle Modified Medium (DMEM Sigma) supplemented with 10% FBS, 1% Glutamax and 1% NGAA. Cells are transfected when 50% confluent, 24 h after seeding (7 million for T-75 flask and 800.000 per well for a 6 well plate). Transfections are performed using Lipofectamine and Plus reagent (Life Technologies, catalog n. 11514 and 18324) according to the manufacturer's instructions.

(B) Plasmid Construction

The TTV NCR is PCR amplified using suitable primers. For example, the TTV-HD14a NCR is PCR amplified using primers TT-ON9 5' gattatggtacctttccaactacgactgggtgt (SEQ ID NO:83) and TT-ON10 5' gattatggtacctctaccattcgtcaccgct-gtt (SEQ ID NO:84) using pCDNA3.1(+)-TTV-HD14a as template (a plasmid containing full-length TTV-HD14a linearized and cloned into XbaI site). PCR product is run on a 1% agarose gel and DNA stained using ethidium bromide. Bands corresponding to the expected size (~1200 bp) are cut and subsequently extracted from agarose using QIAEXII gel extraction kit (QIAGEN). 4 μg of pCDNA3.1(+) (Life technologies) are cut using KpnI and dephosphorylated using FastAP (Thermo scientific). PCR product is cut using the same procedure, but not dephosphorylated. Cut plasmid and PCR products are cleaned up by using QIAEXII gel extraction kit.

Ligation of the plasmid and the amplified fragment corresponding to the TTV NCR, for example TTV-HD14a NCR, is performed using T4DNA ligase (Thermo Scientific) Ligation product is transformed into NovaBlue Singles competent cells (Merck Millipore) according to the manufacturer instructions, and seeded in LB agar plates supplemented with ampicillin as selection marker. Plates are incubated 20 hours at 37° C. Single colonies are picked and seeded in LB medium supplemented with ampicillin. These cultures are incubated 20 hours. Plasmid is extracted using PureLink Quick Plasmid Miniprep Kit (Life technologies). 1 μg of each plasmid are double cut with SacI and NheI (Thermo Scientific). Cut products are run in 1% agarose gels. The restriction strategy allows us to distinguish between inserts clones in the sense and antisense orientation. Two positive plasmids, one containing the sense and the other one the antisense insert, are chosen and sent for sequencing. After confirming the sequence, plasmids are prepared for transfection by using Plasmid Max Kit (Qiagen).

(C) RNA Extraction and DNAse Treatment

Cells are harvested 48-72 h post-transfection. Cells are homogenized using QiaShreder (Qiagen) according to manufacturer instructions. Lysates are then subjected to RNA extraction using miRNAeasy mini kit or RNAeasy mini kit (Qiagen) depending on the purpose of the RNA (for miRNA Northern blot or for RT-qPCR), according to manufacturer instructions.

After elution, RNA samples are treated with RQ1 Dnase (Promega) according to manufacturer instructions, with the addition of RNasin (Promega). Phenol-Chloroform extraction followed by ethanol precipitation is performed, and the resulting pellet is resuspended in DEPC water. RNA quality and concentration are tested using NanoDrop 2000c (Thermo Scientific).

(D) Probes Labeling

Custom DNA oligos are ordered to Sigma (Table 4). Probes are 3' biotin labeled. 10 pmoles of each probe are incubated with 4U of Terminal Deoxynucleotidyl transferase (TdT) and 2,5 nanomoles of Biotin-11-dUTP (Thermo Scientific) in 1×TdT buffer, overnight. Probes are subjected to Isoamyl alcohol-Chloroform extraction and the total volume is used for subsequent hybridization.

(E) Northern Blot 30-50 μg of total RNA per sample are separated by electrophoresis using 15% polyacrylamide (29:1) gels cast in 7M urea and buffered with 1×TBE using a MiniProtean cell (Bio-Rad). The electrophoresis buffer is 0.5×TBE. Gels are stained with EtBr.

For blotting, gels are placed over a sheet of nylon hybridization membrane (Hybond-NX®, Amersham/Pharmacia) pre-wetted in 0.5×TBE. This is then sandwiched between pieces of 3 MM Whatman filter paper (one layer under the membrane and three over the gel), also pre-wetted in 0.5× TBE and placed in a Trans-Blot SD semidry transfer cell (Bio-Rad). Excess liquid and air bubbles are squeezed from the sandwich by rolling the surface with a pipette. Electrophoretic transfer of RNA from the gel to the membrane is carried out at 400 W for 60-90" min. After transfer, RNA is crosslinked to the membrane by ultraviolet exposure using Stratalinker (Stratagene).

Membranes are cut as needed and hybridized with the appropriated biotin labeled probe (Table 4) o/n in Ultrahyb Oligo buffer (Life technologies) at 42° C. After hybridization, 4 washes are performed; the first one with 2×SSC 30 min at 42° C., the second one with 2×SSC 0.5% SDS 30 min at 42° C. and the last two with 2×SSC 0.5% SDS 30 min at 55° C. Hybridization signals are detected using BrightStar BioDetect Kit (Life technologies) according to the manufacturer instructions. Film used: (Fiji).

(F) RT-qPCR

1 μg of RNA is used to make cDNA with superscript III and RnaseOUT (Life technologies) according to manufacturer instructions. cDNA is diluted 1:10. qPCR is performed using Taqman fast master mix and Taqman expression assays, in a qPCR machine StepOne plus (Applied Biosystems).

(G) Pre-miRNA Prediction and Mature miRNA Prediction

V-mir is set to default configuration, changing the sequence type to circular. CID-miRNA is run on the web-based tool, using the default run configuration for *Homo sapiens*. Mature Bayes is run on the web-based tool.

(H) miRNA Target Predictions

DIANA microT 3.0 is run on the web-based tool (no options are given for this program). RNA hybrid is run using constraint nucleotide configuration, from nucleotide 2 to 8 of the miRNA. G:U pairs are allowed.

Table 1

Predicted pre-miRNA from TTV-HD14a using CID-miRNA and V-mir that match three criteria: being predicted by both programs, score over 150 for V-mir and located in the non-coding region of the virus.

TABLE 1

Predicted pre-miRNA from TTV-HD14a using CID-miRNA and V-mir that match three criteria: being predicted by both programs, score over 150 for V-mir and located in the non-coding region of the virus.

| Group | Orientation | Length | Starting nucleotide | Name |
|---|---|---|---|---|
| S2 | sense | 69 | 3135 | TTV-HD14a-mir-1 (SEQ ID NO: 1) |

Sequence and secondary structure
```
          g    ----  a----  a         cu
5'gccuc gacccccc    ucg    cc gaaucg  c
  |||||  ||||||||   |||    || ||||||
3'cgggg cugggggg    ggc    gg cuuagc  g
          g         cucc   gucca -    gc
```

| S3 | Sense | 78 | 3420 | TTV-HD14a-mir-2 (SEQ ID NO: 2) |

Sequence and secondary structure
```
               ac       - a  c      gugua
5'gcugugacguca   gucacgugg gg gga ggc     a
  ||||||||||||   ||||||||| || ||| |||     c
3'cggcacugcagu   cagugcacu cc ccu cug     c
               c-       a  - a      aaggc
```

| AS3 | Antisense | 63 | 3576 | TTV-HD14a-ASmir-1 (SEQ ID NO: 3) |

Sequence and secondary structure
```
        - ac c a--      u      u
5'ccgccg cu gu ac    cuucc cuuuuu u
  ||||||  ||  ||  ||  |||||  ||||||  u
3'ggcggu ga ca ug    gaagg gaaaaa a
        a a- c aag     c      c
```

| AS1 | Antisense | 80 | 3497 | TTV-HD14a-ASmir-2 (SEQ ID NO: 4) |

Sequence and secondary structure
```
    c          -    gau    u    uuc  gg
5'ggc gugacgucag gucacgu   gggga gac  cg u
  |||  ||||||||| |||||||   ||||| |||  || u
3'ccg cacugcaguu cagugca   ccccu cug  gc a
    a          g    ---    c    cc-  ac
```

TABLE 2A

Initial pre-miRNA predicted from different TTV strains grouped according to sequence homology. The predicted mature miRNA are underlined.

| Group | Pre-miRNA Alignment name |
|---|---|
| Sense1 | TTV-HD16a-mir-3                                                                              GGCCGCCATTTT<u>AAGTAA</u>-- <br> <u>GGCGGAAGCAACTCCA</u>CTTTCTCACAAAATGGCGG<u>CGGAGCACTTCCGGCTTGCCCA</u>AAATGGCCGCC (SEQ ID NO: 5) <br> TTV-sle2057-mir1                                                                                       --CCGCCATTTT<u>AAGTAA</u>-- <br> <u>GGCGGAAGCAGCTCCA</u>CTTTCTCACAAAATGGCGG<u>CGGAGCACTTCCGGCTTGCCCA</u>AAATGGCGG-- (SEQ ID NO: 6) <br> TTV-HD23a-mir-1                                                                                        --CCGCCATTTT<u>AAGTAA</u>-- <br> <u>GGCGGAAGCAGCTCCA</u>CCCTCTCACATAATGGCGG<u>CGGAGCACTCCCGGCTTGCCCA</u>AAATGGCGG-- (SEQ ID NO: 7) <br> TTV-Sanban-mir-1                                                                  -GCCGCCATTTT<u>AAGTAA</u>--<u>GGCGGAAGCAGCTCGG</u>CATA-- <br> TACAAAATGTCGG<u>CGGAGCACTTCCGGCTTACCCA</u>AAATGAAGGC- (SEQ ID NO: 8) <br>                      **************** ********* ***    *     ***  ****  *********** <br>    ******* ********    * |

TABLE 2A-continued

Initial pre-miRNA predicted from different TTV strains grouped according to sequence homology. The predicted mature miRNA are underlined.

| Group | Pre-miRNA Alignment name |
|---|---|
| Sense2 | TTV-HD14a-mir-1     GCCTCGGACCCCCCCTCGACC<u>AGAATCGCTCGCGCGATTCGGA</u>CCTG--CGGCCTCGGGGGGGTCGGGGGC (SEQ ID NO: 9)<br>TTV-CT30E-mir-1     -CCTCGGACCCCCCCCCGACCC<u>GAATCGCTCGCGCGATTCGGA</u>CCTG--CGGCCTCGGGGGGGGTCGGGG- (SEQ ID NO: 10)<br>TTV-HD16a-mir-2-    -CCTCGGACCCCCGCTCGTGCTGACGCGCTTGCGCGCGT<u>CAGACCACTTCGGGCTCGCGGGG</u>---------- (SEQ ID NO: 11)<br>                    ************ * ** * **  * ** ***** ** **** *** **** **** |
| Sense3 | TTV-HD14a-mir-2     GCTGTGAC<u>GTCAACG-TCACGTGGG-GAGGAC</u>GGCGTGTAACCCGGAAGT<u>CATCCCCA-TCACGTGACCTGACGTCACGGC</u>-- (SEQ ID NO: 12)<br>TTV-Sanban-mir-2     ------ACGT<u>CACAAGTCACGTGGGGAGGGTT</u>GGCGTATAGCCCGGAAGT<u>CAATCCT-CCCACGTGGCCTGTCACGT</u>------ (SEQ ID NO: 13)<br>TTV-HD23a-mir-2     GCAGCTACGTCA<u>CAAGTCACCTGACTGGGGAGGAGT</u>TACATCCCGGA<u>AGTTCTCCTCGGTCACGTGACTGTACACGTGACTGC</u> (SEQ ID NO: 14)<br>TTV-sle2057-mir-2    ------ACGTC<u>ACAAGTCACCTGACTGGGGAGGAGT</u>CACAACCCGGAAGTC<u>CTCTTCGGTCACGTGACTAGTCACGT</u>------ (SEQ ID NO: 15)<br>                    ****** **** **   ** *   * ********* ****** * |
| AS1 | TTV-HD14a-ASmir-2    ----GGCCGTGA<u>CGT-CAG-GTCACGTGAT-GGGGAT</u>GACTTCCGGGTTACACGCC<u>GTCCTCC-CCACGTGACGT-TGACGTCACAGCC</u> (SEQ ID NO: 16)<br>TTV-CT30E-ASmir-3     -------CGTGACGT-<u>CAGAGTCACGTGACCAGGGATG-CTT</u>CCGGGTTTAGGCACGCCCCCA-TCACGTGTCTC-AAACGTCACG (SEQ ID NO: 17)<br>TTV-HD23a-ASmir-1     GCAGTCACGTGTA---CA--GT<u>CACGTGACCGAGGAGAACTT</u>CCGGGATGTAACTCCTCCCCAGTCAGGTGACTTGTGACGTAGCTGC- (SEQ ID NO: 18)<br>TTV-sle2057-ASmir-1    ------ACGTGAC---<u>TA--GTCACGTGACCGAAGAGGAC</u>TTCCGGGTTGTGACTCCTCCCCAGTCAGGTGACTTGTGACGT------- (SEQ ID NO: 19)<br>TTV-HD16a-ASmir-1     ------ACGTGA<u>C---CA--GTTACGTGGTTGAGGAT-ACTT</u>CAGTGTTTAAGTAC<u>CTCCCCAGTCACGTGACTTATGACGT</u>------- (SEQ ID NO: 20)<br>                    ****  * ** *****    *  **** * * *     ** *<br>** *** *    **** |
| AS2 | TTV-HD16a-ASmir-2    ---GCCA<u>TTTTGGGCAAG</u>--CCG--<u>GAAGTGCT</u>CCGCCGCCATTTTGTGAGAAAGTGGAGT<u>TGCTTCCGCCTTACTTAAAAT</u>GGC--- (SEQ ID NO: 21)<br>TTV-sle2057-ASmir-2   -CCGCCATTTTGGGCAAG--CCG--GAAGTGCTCCGCCGCCATTTTGTGAGAAAGTGGAGC<u>TGCTTCCGCCTTACTTAAAAT</u>GGCGG- (SEQ ID NO: 22)<br>TTV-HD23a-ASmir-2    -CCGCCATTTTGGGCAAG--CCG--GGAGTGCTCCGCCGCCATTATGTGAGAGGGTGG<u>AGCTGCTTCCGCCTTACTTAAAAT</u>GGCGG- (SEQ ID NO: 23)<br>TTV-Sanban-ASmir-2     GCCTTCATTTTGGGTAAG--CCG--GAAGTGCTCCGCCGACATTTTGT--ATATGCCG<u>AGCTGCTTCCGCCTTACTTAAAAT</u>GGCGGC (SEQ ID NO: 24)<br>TTV-tth8-ASmir-2      ----CCATTTT<u>GAGTAGGTGTGGCTGATGGTGA</u>CCTTTGAACTCACGCC<u>ACCGTCCG</u>------<u>CCTCAAC</u>--TACTTAAGATGG---- (SEQ ID NO: 25)<br>TTV-TWH-ASmir-3       ----CCATTTT<u>GTGTAGCTTCCGTCGAGGATGA</u>CCTTTAACCTCTA-CGT<u>CAATCCTGA</u>----CGTCAGC--TACTTAAAATGG---- (SEQ ID NO: 26)<br>                    ******* * * * * ** * *<br>** * ******* **** |
| AS3 | TTV-HD14a-ASmir-1 CCG<u>CCGCTAC-GTCACACTTCCTCTTTTTTT</u>TACAAAAAGC<u>GGAAGGAAGTCACAAGATGGCGG</u> (SEQ ID NO: 27)<br>TTV-CT30E-ASmir-2 CCG<u>CCGCTACTGTCATACTTCCTCTTTTTTTT</u>GAAAAAGC<u>GGAAGGAAGTCACAAGATGGCGG</u><br>                    ********** ******************  ***************************<br>(SEQ ID NO: 28) |
| Pre-miRNA failed to be classified into any group | TTV-Sanban-mir-3<br>GCC<u>GGGGGGGCTGCCGCCCCCCCCGGGG</u>AAAGGGGGGGGCCCCC<u>CCCGGGGGGGGGTTTGCCCCCCC</u>GGC (SEQ ID NO: 29)<br>TTV-CT30E-mir-2<br>GTCGTGAC<u>GTTTGAGACACGTGATGGGGGC</u>GTGCCTAAACCCGGAAGCAT<u>CCCTGGTCACGTGACTCTGACGT</u>CACGGC (SEQ ID NO: 30)<br>TTV-CT30E-mir-3 GC<u>GGGGGGGGCGGCCGCGTTCGCGCGCCGCCCCACCAGG</u>GGG<u>TGCTGCGCGCCCCCCCCCGCGC</u> (SEQ ID NO: 31)<br>TTV-HD16a-mir-1<br>GTGCC<u>TACCTCTTAAGGTCACCAAGCAC</u>TCCGAGCGTCAGCGAGG<u>AGTGCGACCCTTGGGGGTGGGT</u>GC (SEQ ID NO: 32)<br>TTV-HD16a-mir-3<br>GGGCGCCATTTT<u>AAGTAAGGCGGAAGCAACTCC</u>ACTTTCTCACAAAATGG<u>CGGCGGAGCACTTCCGGCTTGCCCAAAAT</u>GGCCGCC (SEQ ID NO: 33)<br>TTV-Sanban-ASmir-1<br>GCC<u>GGGGGGCAAACCCCCCCCC</u>GGGGGGGGCCCCCCCC<u>TTTCCCCGGGGGGGGCGGCAGCCCCCC</u>GGC (SEQ ID NO: 34)<br>TTV-Sanban-ASmir-3<br>CCAGAAGG<u>CGGCGGCCTCGTACTCCTGCTGCC</u>AGTCTTGGC<u>TGCTGGGTACGGGTTTTGGGGCCC</u>TGTCTGG (SEQ ID NO: 35)<br>TTV-CT30E-ASmir-1 |

TABLE 2A-continued

Initial pre-miRNA predicted from different TTV strains grouped according to sequence homology. The predicted mature miRNA are underlined.

| Group | Pre-miRNA Alignment name | |
|---|---|---|
| | | CGCGCATGCGCGGTGGGTTTAGCACGGGGGGGGGCCGGGGGGGCGGAGCCCCCCCGGGGGGGGCCCCGCGCATGCGCG (SEQ ID NO: 36) |
| | TTV-CT30E-ASmir-4 | GGGGGGTCCGAGGCGTCCGGCGCAGCGCGAAGCGCGTAGCGCCGGACCCCGAGGAAGTTGCCCC (SEQ ID NO: 37) |

TABLE 2B

TTV mature miRNA present in the TCGA small RNA sequencing datasets of colon adenocarcinoma with similarity in the nucleotides from 1 to 7 (comprising the seed (nt 2 to 7)) to TTV-HD14a-mir-2-3p. The TTV miRNA are shown in the context of the pre-miRNA sequence. The identical conserved nucleotides from 1 to 7 (comprising the seed (nt 2 to 7)) are boxed. Positions containing identical nucleotides are marked by a (*) and positions containing nucleotides originated by a transition are marked by (°). They are classified in groups according to their pre-miRNA sequence. In all cases, the 3p mature miRNA is underlined. The seed is written in italicized letters. The box 3 contains the consensus sequence for the nucleotides from 1 to 7. A — adenine, T — thymine, C — cytosine, G — guanine, Y — C or T. Seed of a miRNA: nucleotides 2 to 7 of the mature form of the miRNA [80]

| Box | TTV pre-miRNA related to | TTV Sequence | |
|---|---|---|---|
| 1 | TTV-HD14a | HD14a | GCTGTG---ACGTC-AACGTCACGTGGGAGGA---CGGCGTGTAACCCGGAAGTCATCCCC A-TCACGTGAC-CTGACGT-CACGGC 78 (SEQ ID NO: 12) |
| | | sledhdi37.25 | GCTGTG---ACGTA-TCAGTCACGTGGGAAGGG---TGTGCCTTAACCCGGAAG-CATCCCTGGTCACGTGACTGTGACGT-CGCGGC 79 (SEQ ID NO: 38) |
| | | Sleef03.4 | GCTGTG---ACGTA-TCAGTCACGTGGGAAGGG---CGTGCCTTAACCCGGAAG-CATCCCTGGTCACGTGACTGTGACGT-CGCGGC 79 (SEQ ID NO: 39) |
| | | sledhdi36.1 | GCTGTG---ACGTT-TAAGTCACGTGGGCGGGG---CGTGCCTTAACCCGGAAG-CATCCCTGGTCACGTGACTGTGACGT-CGCGGC 79 (SEQ ID NO: 40) |
| 2 | TTV-HD18a | SleDhDi08.11 | GTCGTG---ACGTT-TGAGACACGTGATTGGGG---CGTGCCTAAACCCGGAAG-CATCCCTGGTCACGTGACTCTGACGC-CACGGC 79 (SEQ ID NO: 41) |
| | | sleCqCrr53.25 | GTCGTG---ACGTT-TGAGACACGTGATGGGGG---CGTGCCTAAACCCGGAAG-CATCCCTGGTCACGTGACTCTGACGT-CACGGC 79 (SEQ ID NO: 42) |
| | | SleCsRy90.1K | -TCATCTATACGTCATAAGTCACGTGGGAAGGGGTGTGCCCTTAAACCCGGAAG-CATCCTCGTCCACGTGACTGTGACGTGTATGA- 85 (SEQ ID NO: 43) |
| | | sleef01.1 | -TCATGTGTACGTCATAAGTCACGTGAGAAGGGGCGTGCCTTTAAATTCGGAAG-CATCCTCGTCCACGTGACTGTGACGTGTATGA- 85 (SEQ ID NO: 44) |
| | | HD14b | GCTGTG---ACGTC-AACGTCACGTGGGGAGGA---CGGCGTGTAACCCGGAAGTCATCCTC A-TCACGTGAC-CTGACACGGC 78 (SEQ ID NO: 45) |
| | | | °°°*  ****  * ******° ***  * ° °°****  ******°° °  ******** ***** * |
| | | HD18a | CCATTTTAAGTAAGCTCCACCCAGGACTGACGT-CA-GTGTGAAAGGTCATCCTCGGCGGGAACTTACATGAAA-TGGC 77 (SEQ ID NO: 46) |
| | | SleDhDi40.13 | CCATTTTAAGTAGGTGTCGTCCAGGACTGCTGTTCC-GGGTCAGGGGG CATCCTCGGC-GGAACTTACACAAAA-TGGC 76 (SEQ ID NO: 47) |
| | | sleef49.5 | CCATTTTAAGTAGGTGCCGTCCAGGACTGCTGTTCC-GGGTCAGACGG CATCCTCGGC-GGAACTTACACAAAA-TGGC 76 (SEQ ID NO: 48) |

TABLE 2B-continued

TTV mature miRNA present in the TCGA small RNA sequencing
datasets of colon adenocarcinoma with similarity in the
nucleotides from 1 to 7 (comprising the seed (nt 2 to 7)) to
TTV-HD14a-mir-2-3p . The TTV miRNA are shown in the context of
the pre-miRNA sequence. The identical conserved nucleotides from
1 to 7 (comprising the seed (nt 2 to 7)) are boxed. Positions
containing identical nucleotides are marked by a (*) and
positions containing nucleotides originated by a transition are
marked by (°). They are classified in groups according to their
pre-miRNA sequence. In all cases, the 3p mature miRNA is
underlined. The seed is written in italicized letters. The box 3
contains the consensus sequence for the nucleotides from 1 to 7.
A — adenine, T — thymine, C — cytosine, G — guanine, Y — C or T.
Seed of a miRNA: nucleotides 2 to 7 of the mature form of the miRNA [80]

| Box | TTV pre-miRNA related to | TTV Sequence |
|---|---|---|
| | SleDhDi73.11 | CCATTTTGAGTAGGTGCCGTCCAGGACTCCTGTTCC-GGGTCAGAGGG **CA*TCCTC*GGC-GGAACTTACAC**AAAA-TGGC 76 (SEQ ID NO: 49) |
| | sleef061.3 | CCATTTTAAGTAGGTGCCGTCCAGGACTGCTGTTCC-GGGTCAGAGGG **CA*TCCTC*GGC-GGAACCTGCAC**AAAA-TGGT 76 (SEQ ID NO: 50) |
| | SleDhDi64.20 | CCATTTTAAGTAGGTGCCGTCCAGGACTGCTGTTCC-GGGTCAGAGGG **CA*TCCTC*GGC-GGAACCTACAC**AAAAATGGA 78 (SEQ ID NO: 51) |
| | sleef41.2 | CCATTTTAAGTCAGCTTCGGGGAGGCATGACGTGTA-GT-TCAAAGGT **CA*TCCTC* A-CCGGAACTGGCAC**AAAA-TGGC 75 (SEQ ID NO: 52) |
| | sleDhDi19.1 | CCATTTTAAGTCAACGCTGGGGAGGCGTGACGTACA-GT-TCAAAGGT **CA*TCCTC* G-CCGGAACTGGCAC**AAAA-TGGC 75 (SEQ ID NO: 53) |
| | SleDhDi27.17 | CCATTTTAAGTCAGCGCTGGGGAGGAGTGACGTACA-GT-TCAAAGGT **CA*TCCTC* G-TCGGAACTGGCAC**AAAA-TGGC 75 (SEQ ID NO: 54) |
| | SleCsRx07.9 | CCATTTTAAGTAAGCACCGCCTAGGACTGACGTATAAGT-TCAAAGGT **CA*TCCTC*GGCCGGAACTTACAC**AAAA-TGGT 78 (SEQ ID NO: 55) |
| | | \*\*\*\*\*\*\*\*°\*\*\* ooo ooo \*\*\*o \* o\*\* o \* \* \*oo \* |
| | | \*\*\*\*\*\*\* oo \*\*\*\*\*o o\*\*oo\*\*\* \*\*\* |
| 3 | Consensus sequence for the nucleotides from 1 to 7 (comprising the seed (nt 2-7)) | Common to all the TTV *CATCCYY* |

TABLE 3

Genes predicted to be down-regulated by the TTV-HD14a and at least two other TTV strains miRNA. Notice that some strains have more than one putative miRNA that is predicted to down-regulate some of the genes.

| Gene | NCBI accession number | Number of TTV isolates predicted to down-regulate it | Number of TTV miRNA predicted to down-regulate it |
|---|---|---|---|
| APC2 | NM_005883.2 | 4 (Out of 9) | 8 |
| SOX4 | NM_003107.2 | 3 (Out of 9) | 3 |
| TNRC6B | NM_001162501.1 | 4 (Out of 9) | 7 |
| BNC2 | NM_017637.5 | 3 (Out of 9) | 4 |
| ONECUT2 | NM_004852.2 | 5 (Out of 9) | 7 |
| BCL11a | NM_022893.3 | 3 (Out of 9) | 3 |
| SLIT1 | NM_003061.2 | 3 (Out of 9) | 3 |
| MLL | NM_153827.4 | 5 (Out of 9) | 8 |
| MACF1 | NM_012090.5 | 8 (Out of 9) | 12 |
| DST | NM_001144769.2 | 9 (Out of 9) | 13 |
| CREB5 | NM_182898.2 | 3 (Out of 9) | 3 |
| CHD5 | NM_015557.2 | 3 (Out of 9) | 4 |
| SSRP1 | NM_003146.2 | 3 (Out of 9) | 3 |
| MINK1 | NM_001197104.1 | 5 (Out of 9) | 5 |

TABLE 4

| Probe name | Sequence |
|---|---|
| HD14a-mir-1-5p | 5' agcgattctggtcgagggggggtccgag gc-Probe 56 |
| HD14a-mir-1-3p | 5' gcccccgacccccccgaggccgcaggtc cgaatgcg-Probe 57 |
| HD14a-mir-2-5p | 5' acacgccgtcctccccacgtgacgttga cgtcacagc-Probe 58 |
| HD14a-mir-2-3p | 5' gccgtgacgtcaggtcacgtgatgggga tgacttccg-Probe 59 |
| HD14a-ASmir-1-5p | 5' aagaggaagtgtgacgtagcggcgg-Probe 60 |
| HD14a-ASmir-1-3p | 5' cgccatcttgtgacttccttccgctttt-Probe 61 |
| HD14a-ASmir-2-5p | 5' cggaagtcatccccatcacgtgacctga cgtcacggc-Probe 62 |
| HD14a-ASmir-2-3p | 5' gctgtgacgtcaacgtcacgtggggagg acggcgtgt-Probe 63 |
| hsa-mir-93-5p | 5' cactacctgcacgaacagcactttggag cccccag-Probe 64 |

TABLE 4-continued

Probes

| Probe name | Sequence |
|---|---|
| hsa-mir-93-5p | 5' ccgggggctcgggaagtgctagctcagc agtaggt-Probe 65 |

EXAMPLE 2 miRNA Prediction

Figure 1:
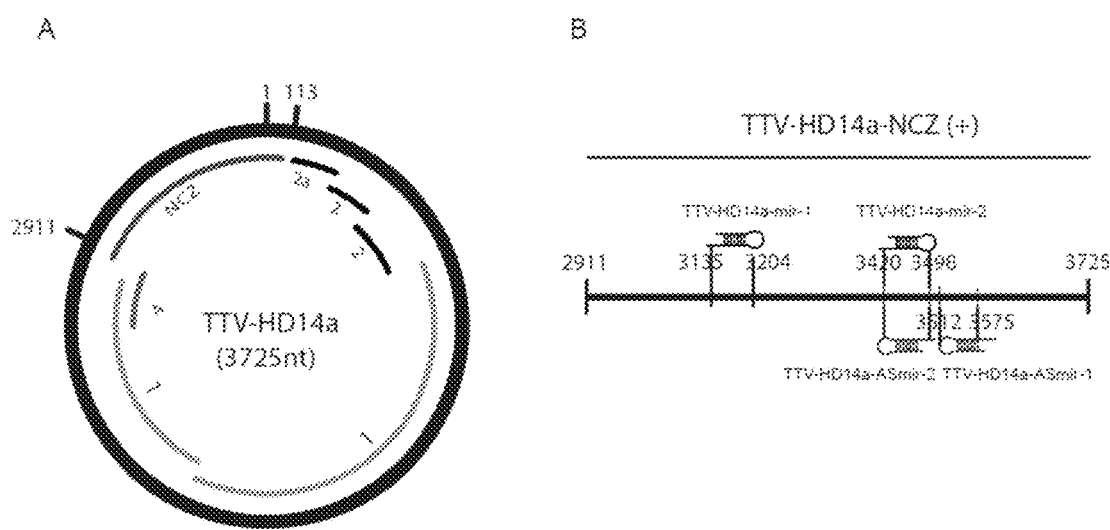
FIG. 1: TTV-HD14a genomic organization and pre-miRNA location (A) TTV-HD14a. The numbers over the lines indicate the nucleotide number. NCR—Non-coding region. (B) Details of the non-coding region. The numbers indicate the nucleotide number. The hairpins over the line indicate the pre-miRNA encoded in sense orientation. The hairpins under the line indicate the pre-miRNA encoded in antisense orientation. The names over and under the hairpins are the names given to the pre-miRNA.

To address the question about the possible function of the non-coding region (NCR) of TTVs beyond its promoter activity, the inventors had the idea that it also generates non-coding RNAs, such as miRNAs. Therefore, they used available miRNA prediction algorithms, with which they identified several candidate pre-miRNAs in the NCR of some TTVs. The inventors chose to use two of such algorithms: CID-miRNA [34] and Vmir [35-36]. The first one was chosen because of its high specificity and the second one because of its higher sensitivity. To consider a pre-miRNA structure as a candidate, they used the criterion that it should be predicted by both programs, with a cut-off value over 125 for the V-mir program and that it had to be located in the NCR of the virus. After filtering, only 4 pre-miRNA candidates (Table 1 and FIG. 1B), two in sense orientation and two in antisense orientation, were considered as putative pre-miRNA and were further evaluated.

In order to check the conservation of the pre-miRNA sequences among different TTV isolates, the inventors performed the same prediction in seven different strains: TTV-HD16a (FR751476, version FR751476.1 GI:339511352, 7 Jul. 2011), TTV-C3T0F (AB064597, version AB064597.1 GI:17827196, 25 Jun. 2008), TTV-HD23a (FR751500, version FR751500.1 GI:339511376, 7 Jul. 2011), TTV-YonKc197 (AB038624, version AB038624.1 GI:7415899, 20 Sep. 2000), TTV-SANBAN (AB025946, version AB025946.2 GI:5572683, 3 Nov. 2009), TTV-Sle2057 (AM712030, version AM712030.1 GI:156104055, 19 Feb. 2008) and TTV-tth8 (AJ620231, version AJ620231.1 GI:49203022, 3 Feb. 2009(GenBank accession numbers and versions in brackets) They then grouped the resulting pre-miRNA in different classes (Table 2A), according to their sequence similarity. As can be observed, the conservation of the sequences is rather poor, being strange the total identity between two pre-miRNA from different strains.

Mature- and pre-miRNAs similar to TTV-HD14a pre-miRNA that contain a mature miRNA with an equal or similar seed to that of TTV-HD14a-3p miRNA which also includes TTV-HD18a-like pre-miRNAs were found within patients by screening TGCA datasets. These miRNAs are shown in Table 2B. The similarity within the nucleotides 1 to 8 of these miRNAs with that of TTV-HD14a miRNAs indicates, that these miRNAs are downregulating APC as well.

EXAMPLE 3

TTV-HD14a can Transcribe Four Precursor miRNA Encoded in its NCR

Figure 2:
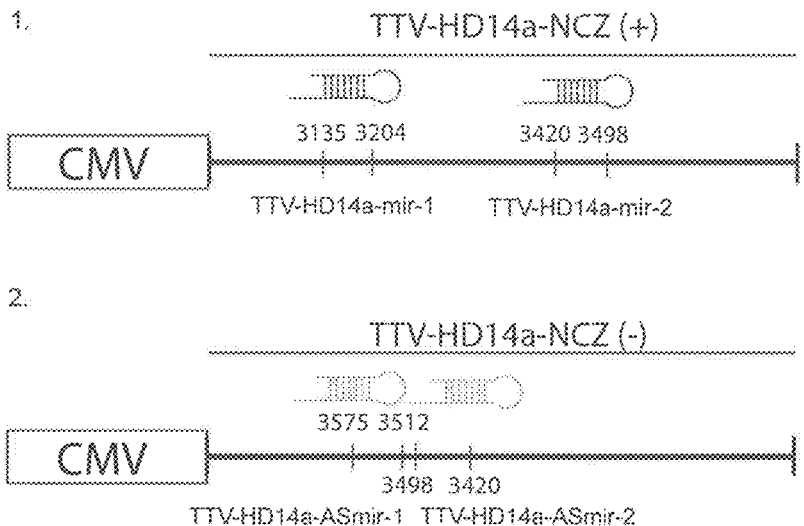
FIG. 2: Schematic representation of the plasmids used for transfection and Northern Blots showing the pre-miRNA and mature miRNA (A) Schematic representation of the plasmids containing the CMV promoter and the non coding region (NCR) in sense (+) or antisense (−) orientation. The constructs are named pCDNA3.1(+)-TTV-HD14a-NCR-Sense and pCDNA3.1(+)-TTV-HD14a-NCR-AntiSense, respectively. The numbers over and under the lines indicate the nucleotide number. The hairpins and the vertical lines indicate the pre-miRNA in sense or antisense orientation. The names of the pre-miRNA are written below the lines.
Figure 2:
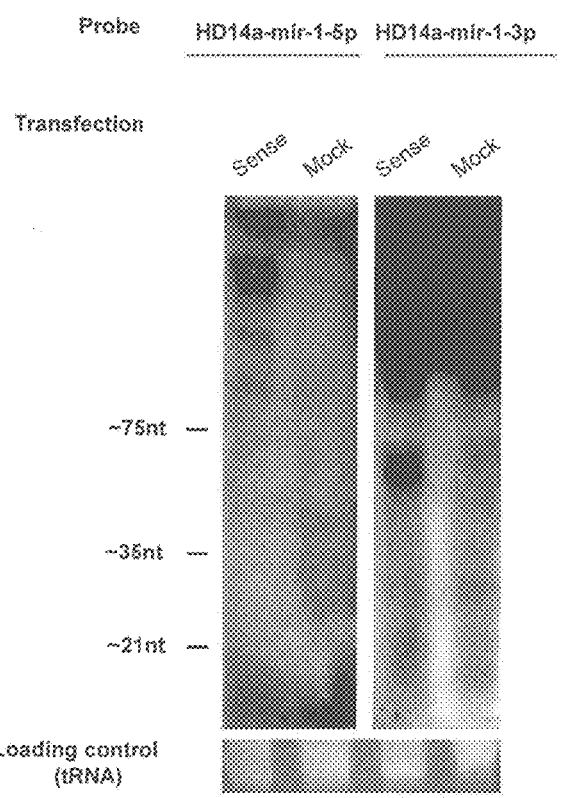
Figure 2:
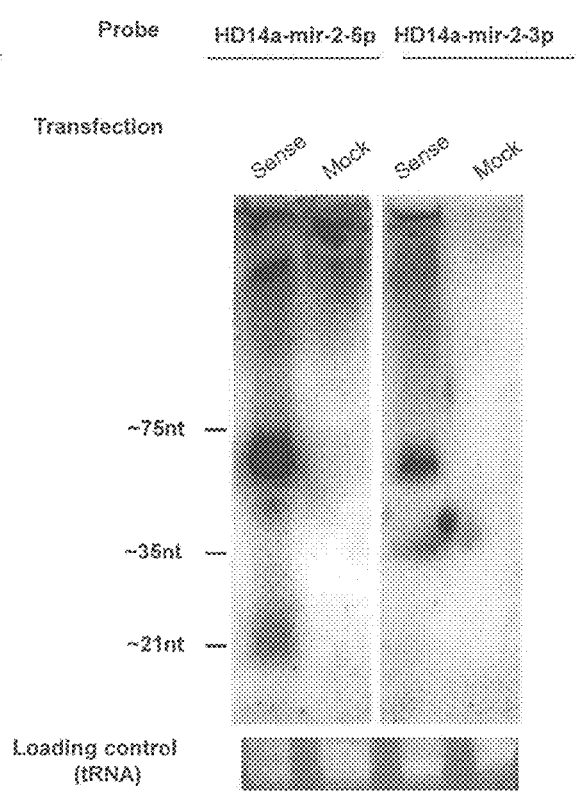

To address the question whether the predicted pre-miR-NAs could be processed, the NCR of TTV-HD14a was cloned downstream of the CMV promoter, in sense or antisense orientation, using the plasmid pCDNA3.1(+)-zeo as scaffold (FIG. 2A). The inventors then transfected HEK293TT cells with these plasmids and performed Northern Blot hybridization with specific probes against the 3' or 5'arm of each putative pre-miRNA (Table 4) (FIG. 2B-E). The inventors could clearly detect bands that match the expected size for a pre-miRNA with the probes directed against the 3' and 5'arm of TTV-HD14a-mir-2 and TTV-HD14a-ASmir-2. Moreover, the inventors were able to detect a transcript matching the expected size for a mature miRNA within the 5'arm of TTV-HD14a-mir-2. On the other hand, the inventors were able to detect transcripts matching the expected sizes with the probes directed against the 3'arm only of TTV-HD14a-mir-1 and TTV-HD14a-ASmir-1.

These results demonstrate that TTV-HD14a encodes for several precursor miRNA in both orientations; and at least one of them can be processed into a mature miRNA.

EXAMPLE 4

Target Prediction

It is well known that the major feature of miRNA is downregulating gene expression in a post-transcriptional manner. It is also known that this effect is caused by the mature form of the miRNAs, and not by their precursors. Although the inventors were not able to see any mature miRNA for three of the pre-miRNA, they think that low expression levels of these miRNAs rather than their absence might be the reason of this. In any case, it is necessary to identify the sequence of the mature miRNA to perform accurate predictions, and this is hard to determine by experimental methods different from miRNA-seq. To overcome this problem, the inventors decided to use an in-silico mature miRNA predictor, Mature Bayes [37]. This program predicts the mature miRNA from a pre-miRNA sequence. After doing that with all the predicted miRNA precursors (Table 2), they used DIANA-microT-3.0 [38-39] to predict possible targets. They reasoned that, despite the variability in their sequences, the putative TTV mature miRNAs should have some targets in common. So, after performing the predictions, the inventors compared the results among the different TTV strains and considered as good candidates the targets that were predicted for some miRNAs belonging to TTV-HD14a and, at least, two more TTV strains. Candidate targets are listed in Table 3.

In addition to this approach, the inventors performed a direct comparison of the predicted mature miRNA from TTV-HD14a with the CDS, 3'UTR and promoter regions of several tumor suppressor genes using RNA Hybrid [40]. This program allows to directly detecting the complementary sequence of a given miRNA within a gene, independently of the conservation or localization of complementary sequence. This is useful, as most of the other prediction programs do not take into account the CDS or promoter region of the genes, while it has been demonstrated that a seed pairing with the first one can mediate PTGS and with the second one can cause TGS or RNAa [11,12,29-33]. The inventors found seed complementarity between the APC gene and TTV-HD14a-mir-2-5p in three different points within the APC mRNA sequence, two in the CDS and one in the 3"UTR (FIG. 3A—1, 2 and 3). In addition, a possible interaction site between TTV-HD14a-mir-2-3p and APC mRNA was present in the CDS (FIG. 3A-4). The inventors also found complementarity between the TTV-HD14a-AS-mir-2-3p and three of the four promoters listed for APC in the Eukaryotic Promoter Database New Human (EPD New Human) [59] (accession names APC_1, APC_2 APC_3 and APC_4) (FIG. 3B-D).

EXAMPLE 5

APC is Down-Regulated after Transfection with pCDNA3.1(+)-TTVHD14a-NCR-Sense

To check the possible APC down-regulation mediated by the TTV-HD14a miRNA the inventors transiently transfected HEK293TT cells with the constructs encoding the miRNA, with the full length TTV-HD14a virus or mock transfected them, followed by RT-qPCR (FIG. 3E+F). APC down-regulation by the miRNA itself as well as by the full length genome (coding for the miRNA) is significant in comparison to the mock transfected.

EXAMPLE 6

GAPDH Up-Regulation by TTV miRNA

After transfection with pCDNA3.1(+)-TTV-HD14a-NCZ-Sense, which is intended to produce 4 mature miRNAs (TTV-HD14a-mir-1-5p, TTV-HD14a-mir-1-3p, TTV-HD14a-mir-2-5p and TTV-HD14a-mir-2-3p), the inventors can observe a statistically significant increase of GAPDH transcript:

GAPDH (Glyceraldehyde-3-phosphate-dehydrogenase) is a gene usually used as internal control (housekeeping gene), at the mRNA and protein levels, because its levels of expression are very constant among very different conditions.

GAPDH is up-regulated in the majority of cancers and under hypoxic conditions [72, 73, 74]. The inventors suggest that the TTV miRNA dependent up-regulation of GAPDH is mediated indirectly by APC down-regulation.

EXAMPLE 7

Microarray Analysis Reveals the Landscape of TTV-HD14a miRNA's Induced Alterations 72 h after transfection of cells with the two different constructs, the full-length TTV HD14a genome or an empty plasmid RNA was isolated and microarray analysis was performed. Table 5 includes all the genes that were consistently deregulated between the transfection with the constructs and with the full-length virus.

TABLE 5

Genes differentially expressed between cells transfected with a plasmid encoding for TTV-HD14a NCR in sense orientation in comparison to mock transfected cells

| ILLUMINA_ID | GENE_SYMBOL | Description |
| --- | --- | --- |
| 5550379 | CAV1 | caveolin 1, caveolae protein, 22 kDa |
| 1230465 | HNRNPK | heterogeneous nuclear ribonucleoprotein K |
| 4230673 | GRM2 | glutamate receptor, metabotropic 2 |
| 7160327 | ARPC2 | actin related protein 2/3 complex, subunit 2, 34 kDa |
| 4640161 | C17orf97 | chromosome 17 open reading frame 97 |
| 2640142 | C17orf97 | chromosome 17 open reading frame 97 |
| 70403 | C14orf45 | chromosome 14 open reading frame 45 |
| 7510097 | CMTM1 | CKLF-like MARVEL transmembrane domain containing 1 |
| 4850736 | CMTM1 | CKLF-like MARVEL transmembrane domain containing 1 |
| 6290358 | TPX2 | TPX2, microtubule-associated, homolog (*Xenopus laevis*) |
| 7150270 | LRRC26 | leucine rich repeat containing 26 |
| 6420441 | LOC728416 | hypothetical LOC728416 |
| 2140541 | LRRC26 | leucine rich repeat containing 26 |
| 6220053 | FAM57B | family with sequence similarity 57, member B |
| 3520128 | TUBG2 | tubulin, gamma 2 |
| 1410470 | FAM71E1 | family with sequence similarity 71, member E1 |
| 2490433 | RNF32 | ring finger protein 32 |
| 650717 | C22orf23 | chromosome 22 open reading frame 23 |
| 4070424 | C16orf93 | chromosome 16 open reading frame 93 |
| 4860068 | STX1A | syntaxin 1A (brain) |
| 2940739 | RASSF1 | Ras association (RalGDS/AF-6) domain family member 1 |
| 2370538 | KRCC1 | lysine-rich coiled-coil 1 |
| 6130047 | CCDC151 | coiled-coil domain containing 151 |
| 1240731 | RFPL3S | RFPL3 antisense RNA (non-protein coding) |
| 650689 | CLIP3 | CAP-GLY domain containing linker protein 3 |
| 7320402 | APBB3 | amyloid beta (A4) precursor protein-binding, family B, member 3 |
| 450204 | ALG9 | asparagine-linked glycosylation 9, alpha-1,2-mannosyltransferase homolog (*S. cerevisiae*) |
| 1240523 | RPL41 | ribosomal protein L41 |
| 1940561 | CGRRF1 | cell growth regulator with ring finger domain 1 |
| 6290609 | RPS15 | ribosomal protein S15 |
| 1090564 | TMEM175 | transmembrane protein 175 |
| 5820494 | ZNF177 | zinc finger protein 177 |
| 7560731 | SNORA64 | small nucleolar RNA, H/ACA box 64 |
| 7550021 | TTC25 | tetratricopeptide repeat domain 25 |
| 2350477 | LRRC6 | leucine rich repeat containing 6 |
| 2480364 | DPP7 | dipeptidyl-peptidase 7 |
| 3180678 | HNRNPH2 | heterogeneous nuclear ribonucleoprotein H2 (H) |
| 3400164 | C21orf2 | chromosome 21 open reading frame 2 |
| 730292 | RNFT2 | ring finger protein, transmembrane 2 |
| 7330474 | MOBP | myelin-associated oligodendrocyte basic protein |
| 6520241 | FAM116B | family with sequence similarity 116, member B |
| 270026 | RASSF1 | Ras association (RalGDS/AF-6) domain family member 1 |
| 5560253 | N6AMT1 | N-6 adenine-specific DNA methyltransferase 1 (putative) |

TABLE 5-continued

Genes differentially expressed between cells transfected with a plasmid encoding for
TTV-HD14a NCR in sense orientation in comparison to mock transfected cells

| ILLUMINA_ID | GENE_SYMBOL | Description |
|---|---|---|
| 3520092 | BAX | BCL2-associated X protein |
| 6940181 | FAM24B | family with sequence similarity 24, member B |
| 7320750 | ILVBL | ilvB (bacterial acetolactate synthase)-like |
| 3840356 | TRIM11 | tripartite motif-containing 11 |
| 6350121 | RASSF1 | Ras association (RalGDS/AF-6) domain family member 1 |
| 7400619 | SPATA5L1 | spermatogenesis associated 5-like 1 |
| 5270343 | IQCC | IQ motif containing C |
| 7320192 | LOC100129148 | hypothetical LOC100129148 |
| 3140689 | KIAA1407 | KIAA1407 |
| 1990593 | IRX6 | iroquois homeobox 6 |
| 5340725 | DYNLRB2 | dynein, light chain, roadblock-type 2 |
| 4120279 | APBB3 | amyloid beta (A4) precursor protein-binding, family B, member 3 |
| 5910397 | LIAS | lipoic acid synthetase |
| 3130035 | FAM149B1 | family with sequence similarity 149, member B1 |
| 2570707 | N6AMT1 | N-6 adenine-specific DNA methyltransferase 1 (putative) |
| 2900725 | CYP27B1 | cytochrome P450, family 27, subfamily B, polypeptide 1 |
| 7400246 | BCDIN3D | BCDIN3 domain containing |
| 5080010 | LOC401431 | hypothetical LOC401431 |
| 830681 | C14orf45 | chromosome 14 open reading frame 45 |
| 5910041 | RPL23AP7 | ribosomal protein L23a pseudogene 7 |
| 1820739 | CDK20 | cyclin-dependent kinase 20 |
| 6350672 | PHF21B | PHD finger protein 21B |
| 1170022 | C17orf81 | chromosome 17 open reading frame 81 |
| 4640095 | RPL9 | ribosomal protein L9 |
| 5390497 | C7orf53 | chromosome 7 open reading frame 53 |
| 4490348 | C9orf6 | chromosome 9 open reading frame 6 |
| 6040156 | C6orf52 | chromosome 6 open reading frame 52 |
| 2480735 | KIAA1731 | KIAA1731 |
| 4180408 | SNORD55 | small nucleolar RNA, C/D box 55 |
| 6660451 | NDUFB4 | NADH dehydrogenase (ubiquinone) 1 beta subcomplex, 4, 15 kDa |
| 4150561 | AASDH | aminoadipate-semialdehyde dehydrogenase |
| 6840291 | FOXN4 | forkhead box N4 |
| 3850754 | KIAA1683 | KIAA1683 |
| 3800400 | LDHAL6B | lactate dehydrogenase A-like 6B |
| 540403 | LRP5L | low density lipoprotein receptor-related protein 5-like |
| 5360139 | LOC100128221 | similar to hCG2041787 |
| 2810674 | TRIM4 | tripartite motif-containing 4 |
| 3780450 | BANP | BTG3 associated nuclear protein |
| 5690280 | FXR2 | fragile X mental retardation, autosomal homolog 2 |
| 1580750 | LOC100130828 | hypothetical LOC100130828 |
| 4610433 | ANGPTL4 | angiopoietin-like 4 |
| 3120452 | MTMR10 | myotubularin related protein 10 |
| 2750465 | C19orf61 | chromosome 19 open reading frame 61 |
| 2470270 | DUS4L | dihydrouridine synthase 4-like (S. cerevisiae) |
| 3370288 | CBX6 | chromobox homolog 6 |
| 7210092 | TRIT1 | tRNA isopentenyltransferase 1 |
| 1580021 | TCTEX1D2 | Tctex1 domain containing 2 |
| 540041 | CASC1 | cancer susceptibility candidate 1 |
| 2030152 | MOBP | myelin-associated oligodendrocyte basic protein |
| 2650678 | RSPH3 | radial spoke 3 homolog (Chlamydomonas) |
| 620414 | HSD17810 | hydroxysteroid (17-beta) dehydrogenase 10 |
| 5360326 | SIP1 | survival of motor neuron protein interacting protein 1 |
| 5860709 | C9orf9 | chromosome 9 open reading frame 9 |
| 5960709 | APITD1 | apoptosis-inducing, TAF9-like domain 1 |
| 6100014 | MRPL47 | mitochondrial ribosomal protein L47 |
| 4150059 | HNRNPH2 | heterogeneous nuclear ribonucleoprotein H2 (H) |
| 5820500 | C1orf35 | chromosome 1 open reading frame 35 |
| 3610148 | EVI5L | ecotropic viral integration site 5-like |
| 3170494 | PPP2R3B | protein phosphatase 2, regulatory subunit B, beta |
| 2810112 | RRAGC | Ras-related GTP binding C |
| 5260692 | ZRSR2 | zinc finger (CCCH type), RNA-binding motif and serine/arginine rich 2 |
| 10543 | PNCK | pregnancy up-regulated non-ubiquitously expressed CaM kinase |
| 940021 | PEX11B | peroxisomal biogenesis factor 11 beta |
| 5340703 | KRCC1 | lysine-rich coiled-coil 1 |
| 70019 | SUGP2 | SURP and G patch domain containing 2 |
| 7150433 | TCTEX1D2 | Tctex1 domain containing 2 |
| 3140634 | MECR | mitochondrial trans-2-enoyl-CoA reductase |
| 4050040 | TUBB3 | tubulin, beta 3 |
| 940576 | ZSCAN21 | zinc finger and SCAN domain containing 21 |
| 4390687 | POMT1 | protein-O-mannosyltransferase 1 |
| 6520687 | SLC7A9 | solute carrier family 7 (cationic amino acid transporter, y + system), member 9 |
| 2750280 | CDK5R1 | cyclin-dependent kinase 5, regulatory subunit 1 (p35) |
| 4210113 | CMTM2 | CKLF-like MARVEL transmembrane domain containing 2 |
| 940435 | TRIM8 | tripartite motif-containing 8 |
| 4850593 | TRIM46 | tripartite motif-containing 46 |

TABLE 5-continued

Genes differentially expressed between cells transfected with a plasmid encoding for
TTV-HD14a NCR in sense orientation in comparison to mock transfected cells

| ILLUMINA_ID | GENE_SYMBOL | Description |
|---|---|---|
| 7550110 | BAX | BCL2-associated X protein |
| 1070541 | MYH3 | myosin, heavy chain 3, skeletal muscle, embryonic |
| 1740576 | LMF2 | lipase maturation factor 2 |
| 6650593 | CEL | carboxyl ester lipase (bile salt-stimulated lipase) |
| 7050326 | CDKN2D | cyclin-dependent kinase inhibitor 2D (p19, inhibits CDK4) |
| 1430673 | SDCBP2 | syndecan binding protein (syntenin) 2 |
| 2600392 | CENPA | centromere protein A |
| 7380634 | C20orf20 | chromosome 20 open reading frame 20 |
| 1740392 | COMMD10 | COMM domain containing 10 |
| 3710746 | OXSM | 3-oxoacyl-ACP synthase, mitochondrial |
| 7550626 | BIRC5 | baculoviral IAP repeat-containing 5 |
| 6020719 | RAB23 | RAB23, member RAS oncogene family |
| 6400524 | LOC390705 | protein phosphatase 2, regulatory subunit B, beta pseudogene |
| 5290148 | GPT2 | glutamic pyruvate transaminase (alanine aminotransferase) 2 |
| 3290296 | MRPS14 | mitochondrial ribosomal protein S14 |
| 770044 | FBXO15 | F-box protein 15 |
| 380079 | SPATA7 | spermatogenesis associated 7 |
| 4590154 | ZDHHC8 | zinc finger, DHHC-type containing 8 |
| 6770673 | SOCS2 | suppressor of cytokine signaling 2 |
| 3940309 | CDAN1 | congenital dyserythropoietic anemia, type I |
| 1470348 | RAGE | renal tumor antigen |
| 3990259 | TMEM91 | transmembrane protein 91 |
| 730475 | PIN4 | protein (peptidylprolyl cis/trans isomerase) NIMA-interacting, 4 (parvulin) |
| 5670075 | PAFAH1B1 | platelet-activating factor acetylhydrolase 1b, regulatory subunit 1 (45 kDa) |
| 4670082 | RGS5 | regulator of G-protein signaling 5 |
| 7210438 | ATRIP | ATR interacting protein |
| 7000333 | ASB6 | ankyrin repeat and SOCS box-containing 6 |
| 3420180 | ZNF202 | zinc finger protein 202 |
| 2760181 | COQ3 | coenzyme Q3 homolog, methyltransferase (S. cerevisiae) |
| 3120093 | EFCAB6 | EF-hand calcium binding domain 6 |
| 3140202 | MYPOP | Myb-related transcription factor, partner of profilin |
| 7380670 | MYB | v-myb myeloblastosis viral oncogene homolog (avian) |
| 6100609 | UAP1L1 | UDP-N-acetylglucosamine pyrophosphorylase 1-like 1 |
| 6520059 | SNF8 | SNF8, ESCRT-II complex subunit, homolog (S. cerevisiae) |
| 6350070 | SCNM1 | sodium channel modifier 1 |
| 430402 | ABCA3 | ATP-binding cassette, sub-family A (ABC1), member 3 |
| 6580402 | UBE2H | ubiquitin-conjugating enzyme E2H (UBC8 homolog, yeast) |
| 6280482 | NIP7 | nuclear import 7 homolog (S. cerevisiae) |
| 4260609 | C2orf74 | chromosome 2 open reading frame 74 |
| 6100056 | HSD17810 | hydroxysteroid (17-beta) dehydrogenase 10 |
| 3890561 | IFT20 | intraflagellar transport 20 homolog (Chlamydomonas) |
| 5900491 | ZNF34 | zinc finger protein 34 |
| 4730204 | FCRLB | Fc receptor-like B |
| 450309 | DDX49 | DEAD (Asp-Glu-Ala-Asp) box polypeptide 49 |
| 2060274 | PREB | prolactin regulatory element binding |
| 4890692 | LOC285943 | hypothetical protein LOC285943 |
| 3130326 | MSH5 | mutS homolog 5 (E. coli) |
| 3440403 | DHDDS | dehydrodolichyl diphosphate synthase |
| 1170121 | MRPL4 | mitochondrial ribosomal protein L4 |
| 2600470 | WDR60 | WD repeat domain 60 |
| 1690711 | SNAPC2 | small nuclear RNA activating complex, polypeptide 2, 45 kDa |
| 5080367 | CKLF | chemokine-like factor |
| 730414 | APOE | apolipoprotein E |
| 3290446 | RPL36 | ribosomal protein L36 |
| 5900286 | ZFP90 | zinc finger protein 90 homolog (mouse) |
| 7610079 | HSF2BP | heat shock transcription factor 2 binding protein |
| 4480477 | SBSN | Suprabasin |
| 540519 | NAGLU | N-acetylglucosaminidase, alpha |
| 6020209 | CYTSA | cytospin A |
| 6100072 | DENND2A | DENN/MADD domain containing 2A |
| 4890382 | ILVBL | ilvB (bacterial acetolactate synthase)-like |
| 2810082 | C20orf111 | chromosome 20 open reading frame 111 |
| 5220309 | RILPL1 | Rab interacting lysosomal protein-like 1 |
| 7040609 | SIP1 | survival of motor neuron protein interacting protein 1 |
| 520446 | COMT | catechol-O-methyltransferase |
| 4670021 | NPEPL1 | aminopeptidase-like 1 |
| 2850180 | NUDT16L1 | nudix (nucleoside diphosphate linked moiety X)-type motif 16-like 1 |
| 650048 | MOBP | myelin-associated oligodendrocyte basic protein |
| 3170725 | C2orf79 | chromosome 2 open reading frame 79 |
| 7210767 | GAK | cyclin G associated kinase |
| 240035 | RUNDC3B | RUN domain containing 3B |
| 1770519 | PDRG1 | p53 and DNA-damage regulated 1 |
| 2190743 | RBM23 | RNA binding motif protein 23 |
| 6620601 | ZBTB40 | zinc finger and BTB domain containing 40 |
| 3140280 | C9orf6 | chromosome 9 open reading frame 6 |

TABLE 5-continued

Genes differentially expressed between cells transfected with a plasmid encoding for
TTV-HD14a NCR in sense orientation in comparison to mock transfected cells

| ILLUMINA_ID | GENE_SYMBOL | Description |
| --- | --- | --- |
| 1820711 | LOC100288144 | hypothetical LOC100288144 |
| 6420632 | MCCC1 | methylcrotonoyl-CoA carboxylase 1 (alpha) |
| 2760519 | CKLF | chemokine-like factor |
| 2490333 | ZNF467 | zinc finger protein 467 |
| 3890274 | DPF2 | D4, zinc and double PHD fingers family 2 |
| 4010452 | SLC38A6 | solute carrier family 38, member 6 |
| 5720154 | ZBTB48 | zinc finger and BTB domain containing 48 |
| 6960692 | ZSCAN10 | zinc finger and SCAN domain containing 10 |
| 6580075 | TAF1D | TATA box binding protein (TBP)-associated factor, RNA polymerase I, D, 41 kDa |
| 1580402 | SLC35B2 | solute carrier family 35, member B2 |
| 6200561 | CCDC28B | coiled-coil domain containing 28B |
| 1780095 | RPL26L1 | ribosomal protein L26-like 1 |
| 2100189 | KCTD13 | potassium channel tetramerisation domain containing 13 |
| 7610538 | H1FX | H1 histone family, member X |
| 6200253 | THBS4 | thrombospondin 4 |
| 3930170 | CDK20 | cyclin-dependent kinase 20 |
| 6560750 | UBE3C | ubiquitin protein ligase E3C |
| 870376 | C9orf152 | chromosome 9 open reading frame 152 |
| 4490544 | LY6G6D | lymphocyte antigen 6 complex, locus G6D |
| 1990674 | NUP50 | nucleoporin 50 kDa |
| 240750 | TELO2 | TEL2, telomere maintenance 2, homolog (S. cerevisiae) |
| 2630102 | CCDC28B | coiled-coil domain containing 28B |
| 7040131 | DALRD3 | DALR anticodon binding domain containing 3 |
| 6480209 | RRAGD | Ras-related GTP binding D |
| 6580521 | UBAC2 | UBA domain containing 2 |
| 7570315 | MRPL45 | mitochondrial ribosomal protein L45 |
| 6510397 | WDR19 | WD repeat domain 19 |
| 610735 | LRRC43 | leucine rich repeat containing 43 |
| 2190241 | AP1M1 | adaptor-related protein complex 1, mu 1 subunit |
| 510370 | SYCE2 | synaptonemal complex central element protein 2 |
| 2360138 | ATP6V0C | ATPase, H + transporting, lysosomal 16 kDa, V0 subunit c |
| 4610201 | SNORA10 | small nucleolar RNA, H/ACA box 10 |
| 3180445 | C14orf79 | chromosome 14 open reading frame 79 |
| 4890647 | C1orf25 | chromosome 1 open reading frame 25 |
| 2810400 | KLHL3 | kelch-like 3 (Drosophila) |
| 540221 | NOP2 | NOP2 nucleolar protein homolog (yeast) |
| 6020458 | NR2F2 | nuclear receptor subfamily 2, group F, member 2 |
| 10626 | TRNAU1AP | tRNA selenocysteine 1 associated protein 1 |
| 3060092 | LAT2 | linker for activation of T cells family, member 2 |
| 1850612 | PARP2 | poly (ADP-ribose) polymerase 2 |
| 3450542 | ECM1 | extracellular matrix protein 1 |
| 4920537 | POLA2 | polymerase (DNA directed), alpha 2 (70 kD subunit) |
| 4760433 | C16orf7 | chromosome 16 open reading frame 7 |
| 3390373 | TIMM22 | translocase of inner mitochondrial membrane 22 homolog (yeast) |
| 3710685 | CARD9 | caspase recruitment domain family, member 9 |
| 7100079 | PHF8 | PHD finger protein 8 |
| 150315 | C21orf7 | chromosome 21 open reading frame 7 |
| 6040703 | TRIM39 | tripartite motif-containing 39 |
| 6650451 | MYCBP2 | MYC binding protein 2 |
| 2750324 | PRKCZ | protein kinase C, zeta |
| 7400707 | C1S | complement component 1, s subcomponent |
| 1070474 | POC5 | POC5 centriolar protein homolog (Chlamydomonas) |
| 2350221 | TSNAXIP1 | translin-associated factor X interacting protein 1 |
| 2630561 | RPL6 | ribosomal protein L6 |
| 6330440 | MSH5 | mutS homolog 5 (E. coli) |
| 4280048 | WFDC3 | WAP four-disulfide core domain 3 |
| 4860367 | ATRIP | ATR interacting protein |
| 1990196 | DACT3 | dapper, antagonist of beta-catenin, homolog 3 (Xenopus laevis) |
| 4120427 | PDX1 | pancreatic and duodenal homeobox 1 |
| 240333 | ETS1 | v-ets erythroblastosis virus E26 oncogene homolog 1 (avian) |
| 4850300 | ARHGAP39 | Rho GTPase activating protein 39 |
| 1710639 | RBM4B | RNA binding motif protein 4B |
| 6620278 | ADI1 | acireductone dioxygenase 1 |
| 3930577 | HMGN2 | high-mobility group nucleosomal binding domain 2 |
| 2490377 | C17orf71 | chromosome 17 open reading frame 71 |
| 4850632 | ALG8 | asparagine-linked glycosylation 8, alpha-1,3-glucosyltransferase homolog (S. cerevisiae) |
| 1780450 | ASB6 | ankyrin repeat and SOCS box-containing 6 |
| 2710546 | COG4 | component of oligomeric golgi complex 4 |
| 6620634 | UBE2S | ubiquitin-conjugating enzyme E2S |
| 5310358 | TIA1 | TIA1 cytotoxic granule-associated RNA binding protein |
| 3610735 | F12 | coagulation factor XII (Hageman factor) |
| 1500678 | TFPT | TCF3 (E2A) fusion partner (in childhood Leukemia) |
| 5220152 | TMEM55B | transmembrane protein 55B |
| 4260441 | CLEC3B | C-type lectin domain family 3, member B |

TABLE 5-continued

Genes differentially expressed between cells transfected with a plasmid encoding for
TTV-HD14a NCR in sense orientation in comparison to mock transfected cells

| ILLUMINA_ID | GENE_SYMBOL | Description |
|---|---|---|
| 610358 | PGS1 | phosphatidylglycerophosphate synthase 1 |
| 6350181 | LOC730183 | hypothetical protein LOC730183 |
| 2100209 | FAM24B | family with sequence similarity 24, member B |
| 1070053 | SUGP2 | SURP and G patch domain containing 2 |
| 4590424 | PDCD2L | programmed cell death 2-like |
| 2470296 | ZSCAN16 | zinc finger and SCAN domain containing 16 |
| 1340411 | CAMSAP1 | calmodulin regulated spectrin-associated protein 1 |
| 4210500 | PSG4 | pregnancy specific beta-1-glycoprotein 4 |
| 6100196 | ZNF653 | zinc finger protein 653 |
| 270053 | GABPA | GA binding protein transcription factor, alpha subunit 60 kDa |
| 6770097 | UBTD1 | ubiquitin domain containing 1 |
| 4220184 | LOC100289410 | hypothetical LOC100289410 |
| 7330674 | KIFC1 | kinesin family member C1 |
| 3400202 | GPATCH1 | G patch domain containing 1 |
| 4900044 | CDC7 | cell division cycle 7 homolog (S. cerevisiae) |
| 1470379 | CCDC116 | coiled-coil domain containing 116 |
| 650626 | C16orf68 | chromosome 16 open reading frame 68 |
| 1300521 | INSM2 | insulinoma-associated 2 |
| 2340180 | TAGLN2 | transgelin 2 |
| 2370064 | ASGR1 | asialoglycoprotein receptor 1 |
| 1070360 | APITD1 | apoptosis-inducing, TAF9-like domain 1 |
| 10075 | ZNF768 | zinc finger protein 768 |
| 5260639 | ZNF330 | zinc finger protein 330 |
| 5360682 | IL17F | interleukin 17F |
| 7570500 | COQ5 | coenzyme Q5 homolog, methyltransferase (S. cerevisiae) |
| 3190246 | CHN2 | chimerin (chimaerin) 2 |
| 6350626 | CCDC120 | coiled-coil domain containing 120 |
| 6330358 | C9orf98 | chromosome 9 open reading frame 98 |
| 3800068 | GTF2E1 | general transcription factor IIE, polypeptide 1, alpha 56 kDa |
| 6180598 | NDUFAF1 | NADH dehydrogenase (ubiquinone) 1 alpha subcomplex, assembly factor 1 |
| 4850674 | PSAT1 | phosphoserine aminotransferase 1 |
| 6590520 | ZNF839 | zinc finger protein 839 |
| 1090687 | POLR1D | polymerase (RNA) I polypeptide D, 16 kDa |
| 2680020 | DAGLB | diacylglycerol lipase, beta |
| 3440315 | PPP2R3B | protein phosphatase 2, regulatory subunit B, beta |
| 4260731 | STMN1 | stathmin 1 |
| 1450707 | RING1 | ring finger protein 1 |
| 380373 | BANP | BTG3 associated nuclear protein |
| 5900112 | ZNF830 | zinc finger protein 830 |
| 7160414 | C7orf63 | chromosome 7 open reading frame 63 |
| 4570500 | CPNE1 | copine I |
| 2060427 | SBDSP1 | Shwachman-Bodian-Diamond syndrome pseudogene 1 |
| 4570292 | PHF12 | PHD finger protein 12 |
| 3710068 | WARS | tryptophanyl-tRNA synthetase |
| 4260044 | SQSTM1 | sequestosome 1 |
| 730687 | TCHP | trichoplein, keratin filament binding |
| 4900431 | STUB1 | STIP1 homology and U-box containing protein 1 |
| 6290239 | ATP6V1B1 | ATPase, H + transporting, lysosomal 56/58 kDa, V1 subunit B1 |
| 6620669 | C3orf23 | chromosome 3 open reading frame 23 |
| 5080431 | NBPF3 | neuroblastoma breakpoint family, member 3 |
| 510112 | PTAFR | platelet-activating factor receptor |
| 3520746 | MTTP | microsomal triglyceride transfer protein |
| 7560328 | RAVER1 | ribonucleoprotein, PTB-binding 1 |
| 3930754 | PRR3 | proline rich 3 |
| 2000100 | ABI2 | abl-interactor 2 |
| 5270239 | TUBD1 | tubulin, delta 1 |
| 460768 | LOC285943 | hypothetical protein LOC285943 |
| 5700722 | TSSC1 | tumor suppressing subtransferable candidate 1 |
| 1190129 | SLMO2 | slowmo homolog 2 (Drosophila) |
| 1400601 | TOX2 | TOX high mobility group box family member 2 |
| 520114 | PET112L | PET112-like (yeast) |
| 5900020 | C10orf110 | chromosome 10 open reading frame 110 |
| 5860452 | BNIP1 | BCL2/adenovirus E1B 19 kDa interacting protein 1 |
| 6350075 | CENPBD1 | CENPB DNA-binding domains containing 1 |
| 4850296 | HCFC1 | host cell factor C1 (VP16-accessory protein) |
| 5050735 | TMEM62 | transmembrane protein 62 |
| 3310681 | LOC391578 | MAF1 homolog (S. cerevisiae) pseudogene |
| 7050612 | TIAM2 | T-cell lymphoma invasion and metastasis 2 |
| 10187 | CNPY3 | canopy 3 homolog (zebrafish) |
| 3890398 | WBP2 | WW domain binding protein 2 |
| 4860184 | PCBD1 | pterin-4 alpha-carbinolamine dehydratase/dimerization cofactor of hepatocyte nuclear factor 1 alpha |
| 130037 | PHF5A | PHD finger protein 5A |
| 6350292 | C1orf50 | chromosome 1 open reading frame 50 |
| 6420296 | MRPL2 | mitochondrial ribosomal protein L2 |

TABLE 5-continued

Genes differentially expressed between cells transfected with a plasmid encoding for
TTV-HD14a NCR in sense orientation in comparison to mock transfected cells

| ILLUMINA_ID | GENE_SYMBOL | Description |
|---|---|---|
| 7510687 | SRCAP | Snf2-related CREBBP activator protein |
| 5820333 | RPUSD2 | RNA pseudouridylate synthase domain containing 2 |
| 2190010 | RACGAP1 | Rac GTPase activating protein 1 |
| 2570288 | SH3YL1 | SH3 domain containing, Ysc84-like 1 (*S. cerevisiae*) |
| 2070201 | CCKBR | cholecystokinin B receptor |
| 1570129 | TRAFD1 | TRAF-type zinc finger domain containing 1 |
| 610670 | ISL2 | ISL LIM homeobox 2 |
| 6370593 | BCL7B | B-cell CLL/lymphoma 7B |
| 4860291 | HMGXB3 | HMG box domain containing 3 |
| 2360601 | NAA25 | N(alpha)-acetyltransferase 25, NatB auxiliary subunit |

With these genes also Gene ontology analyses were performed. The results are shown in Table 6. As can be seen, TTV miRNA might be deregulating several pathways important for cancer progression.

TABLE 6

Gene enrichment analysis

| Category | Term | Genes | Count | % | P-Value |
|---|---|---|---|---|---|
| SP_PIR_KEYWORDS | ribosomal protein | | 12 | 0.4 | 4.4E−4 |
| SP_PIR_KEYWORDS | alternative splicing | | 159 | 5.0 | 7.4E−4 |
| SP_PIR_KEYWORDS | ribonucleoprotein | | 14 | 0.4 | 1.2E−3 |
| SP_PIR_KEYWORDS | coiled coil | | 54 | 1.7 | 1.3E−3 |
| SP_PIR_KEYWORDS | zinc-finger | | 46 | 1.4 | 3.2E−3 |
| SP_PIR_KEYWORDS | nucleus | | 95 | 3.0 | 5.5E−3 |
| SP_PIR_KEYWORDS | cell cycle | | 17 | 0.6 | 6.5E−3 |
| SP_PIR_KEYWORDS | microtubule | | 11 | 0.3 | 7.0E−3 |
| SP_PIR_KEYWORDS | s-adenosyl-1-methionine | | 6 | 0.2 | 3.3E−2 |
| SP_PIR_KEYWORDS | chromosomal protein | | 7 | 0.2 | 4.0E−2 |
| SP_PIR_KEYWORDS | ligase | | 11 | 0.3 | 4.0E−2 |
| SP_PIR_KEYWORDS | cell division | | 10 | 0.3 | 4.0E−2 |
| SP_PIR_KEYWORDS | cytoplasm | | 71 | 2.2 | 4.2E−2 |
| SP_PIR_KEYWORDS | williams-beuren syndrome | | 3 | 0.1 | 4.6E−2 |
| SP_PIR_KEYWORDS | zinc | | 49 | 1.5 | 4.9E−2 |
| SP_PIR_KEYWORDS | mitochondrion | | 22 | 0.7 | 5.3E−2 |
| SP_PIR_KEYWORDS | transit peptide | | 14 | 0.4 | 7.1E−2 |

TABLE 6-continued

Gene enrichment analysis

| Category | Term | Genes | Count | % | P-Value |
|---|---|---|---|---|---|
| SP_PIR_KEYWORDS | acetylation | | 56 | 1.7 | 7.6E−2 |
| SP_PIR_KEYWORDS | plasma | | 5 | 0.2 | 7.7E−2 |

EXAMPLE 8

Screening the TCGA for TTV miRNA Associated with Cancer

The TCGA (The Cancer Genome Atlas) is an initiative of the NIH. The data stored within this repository consist of sequencing datasets from cancer and normal tissue extracted from patients. In this regard, the data extracted by this analysis can be considered as "in vivo", since it comes directly from tumors of patients. In an effort to establish a relationship between TTV miRNA and cancer, the small-RNA sequencing data for colon adenocarcinoma, lung adenocarcinoma, breast carcinoma and hepatocellular carcinoma from the TCGA initiative was mapped against all the full-length TTV genomes included in the NCBI database plus several newly identified TTV from the inventors's laboratory. To exclude artifacts, miRNA taken into consideration complied to the following: mapping with 2 mismatches or less to TTV genomes and mapping in a region where the RNA is predicted to acquire the characteristic hairpin structure of a pre-miRNA (Table 7).

TABLE 7

Small RNA sequencing datasets from patients with different malignancies were screened for
the presence of TTV miRNA. TTV positive patients were considered when having at least
one read mapping to a TTV miRNA. Patients positive for TTV encoding a mature miRNA
presenting the "consensus sequence" where considered when having at least one read
mapping to a TTV strain that encodes for a mature miRNA that contains the "consensus
sequence". The "consensus sequence", the TTV strains found in the TCGA containing the
consensus sequence and the mature miRNA form these TTV strains are listed in Table 2B.+

| Cancer type | Total number of patients screened | TTV positive patients | % of TTV positive patients | Patients positive for TTV encoding a mature miRNA presenting the "consensus sequence" | % |
|---|---|---|---|---|---|
| Colon carcinoma | 421 | 76 | 18,05225653 | 53 | 12,5890736 |
| Hepatocellular carcinoma | 147 | 19 | 12,92517007 | 9 | 6,12244898 |
| Lung adenocarcinoma (Ongoing) | 213 | 25 | 11,7370892 | 9 | 4,22535211 |

TABLE 7-continued

Small RNA sequencing datasets from patients with different malignancies were screened for the presence of TTV miRNA. TTV positive patients were considered when having at least one read mapping to a TTV miRNA. Patients positive for TTV encoding a mature miRNA presenting the "consensus sequence" where considered when having at least one read mapping to a TTV strain that encodes for a mature miRNA that contains the "consensus sequence". The "consensus sequence", the TTV strains found in the TCGA containing the consensus sequence and the mature miRNA form these TTV strains are listed in Table 2B.+

| Cancer type | Total number of patients screened | TTV positive patients | % of TTV positive patients | Patients positive for TTV encoding a mature miRNA presenting the "consensus sequence" | % |
|---|---|---|---|---|---|
| Breast carcinoma(ongoing) | 141 | 11 | 7,80141844 | 1 | 0,70921986 |

TTV-HD14a-2-3p analogous miRNA (meaning, with 80% homology or more in the nucleotides from 1 to 7 of the miRNA, comprising the seed) (Table 2B) were found at higher frequency in colon cancer patients than in the other three type of cancer being screened so far.

The slight differences in the seed of the miRNA shown in Table 2B in respect to TTV-HD14a-mir-2-3p do not alter the predicted binding sites in APC mRNA. Thus, the miRNA shown in Table 2Bare also able to down-regulate APC (Table 8).

Table 8

It is shown how, despite the single nucleotide polymorphisms (SNP) found in the seed of diverse TTV miRNA's respect to the TTV-HD14a-mir-2-3p seed, the predicted interaction site with APC mRNA shown in FIG. 3 (A.4) would be conserved. (B) Here the inventors show how the most conserved seed motif (AUCCUC) has three additional possible interaction sites within APC mRNA in addition to the previously described for TTV-HD14a-mir-2-3p.

Positions are shown in relation to the nucleotide number of APC transcript variant 2 mRNA (NCBI accession number: NM 001127510.2, SEQ ID NO:82)

Seed interaction sites are shown in black bold letters. Sequence corresponding to APC mRNA are shown in italicized letters.

TABLE 8

Extrablatt

A- Conserved interaction site within APC miRNA of the TTV mRNA's containg a similar seed to TTV-HD14a-mir-2-3p

| Seed Sequences | Position within APC mRNA (gi\|306922385/ref\| NM_001127510.21) | Interaction sites |
|---|---|---|
| AUCCCU | nt 5049-5069 | APC   5' U  UU    ---      G       A 3'<br>             AG  UUAC  ACCG GGGAUG (SEQ ID NO: 66)<br>             UC  AGUG  UGGU CCCUAC (SEQ ID NO: 67)<br>miRNA 3' -  UC   CAC      -       5' |
| AUCCUC | nt 5045-5069 | APC   5' A   U      ACA    G       A 3'<br>             UGU AGUUUU  CCG GGGAUG (SEQ ID NO: 68)<br>miRNA    ACA GCAAGG   GGC UCCUAC (SEQ ID NO: 69)<br>       3' AC  U       C--        - 5' |

B- Additional interaction sites with APC mRNA created by the transition of the fifth nucleotide of the TTV-HD14a-mir-2-36 seed from C to T(U)

| Seed Sequences | Position within APC mRNA (gi\|306922385/ref\| NM_001127510.21) | Interaction sites |
|---|---|---|
| AUCCUC | nt 10347-10360 | APC   5' ----------A   CA         A 3'<br>                   GAU  GAGGGUG (SEQ ID NO: 70)<br>                   CUA  CUCCUAC (SEQ ID NO: 71)<br>miRNA 3' AGUCCAGUGCA   --         5' |
| AUCCUC | nt 7890-7925 | APC   5' A    AAUCCA    AAAAGCAAAAAG       A 3'<br>              UCAG      GUGA            UGAGGAUG (SEQ ID NO: 72)<br>              AGUC      CACU            ACUCCUAC (SEQ ID NO: 73)<br>miRNA 3' -     CAGUG     ------------       5' |
| AUCCUC | nt 8099-8129 | APC   5' -U  -  C  CUGUUUCUAAACA        U- 3'<br>              GG CAC UG                 GAGGAUG (SEQ ID NO: 74)<br>              CC GUG AC                 CUCCUAC (SEQ ID NO: 75)<br>miRNA 3' GU  A   C  UA-----------         5' |

This supports a causal role for this type of TTV miRNA of Table 2B in this disease or, at least, an association between them.

A significant increase in TTV load in cancer patients compared to normal controls has been demonstrated [44]. In the case of colon cancer, this increase in viral load would presumably be represented mainly by the TTV strains encoding for miRNA analogous to that of TTV-HD14a.

EXAMPLE 9

Wnt Activation by a TTV miRNA

APC exerts its tumor suppressor activity by downregulating canonical Wnt pathway, although other putative roles for this protein have been suggested. This effect is mediated by its participation in the "destruction complex". The destruction complex is formed by APC, AXIN, and GSK3-beta, among others. This complex phosphorylates beta-catenin, allowing its ubiquitination and degradation by the proteasome. In the absence of any of the proteins of the destruction complex, its function is impaired. The final outcome is the cytoplasmic accumulation of beta-catenin, that can be then translocated into the nucleus, where it activates transcription of its target genes, together with the transcription factor TCF4 or LEF1. It is well documented that this pathway is upregulated in several malignancies, as well as in other diseases. Consequently, we thought that the APC down-regulation could lead to an activation of Wnt pathway. To check this, a gene reporter approach was used. HEK293TT cells were transfected with the plasmids encoding for TTV-HD14a miRNA, with the TTV-HD14a full genome, or mock transfected, together with a plasmid encoding for *Firefly luciferase* under the control of a minimum promoter and seven binding sites for the TCF4/beta catenin complex (TOPFLASH plasmid). Additionally, *Renilla Luciferase* under the control of CMV promoter was used for normalization purposes. An upregulation of wnt pathway resulted in cells with the plasmid encoding for the sense-miRNA or with the TTV-HD14a virus in comparison to mock transfected cells (FIG. 5).

CONCLUSIONS

The above results highlight the importance of the experimental findings as diagnostic method for TTV infection and identifies TTV miRNA as promising target for cancer prevention, treatment or recurrence.

It is known that TTV replicate in several tissues [21], but they only replicate in peripheral blood mononuclear cells when these cells are activated [42]. It was recently demonstrated that TTV replicate more efficiently when they are co-infecting cells with Epstein Barr virus [41].

Very few things are known about the molecular mechanisms mediating infection, replication and virus-host interaction of the TTVs. Here, the inventors provide evidence which supports that several TTVs encode miRNA and that some of them have a biologically relevant role, especially in relation to cancer development.

It has been shown in the present invention that the encoded miRNA of TTV-HD14a and Table 2B can down-regulate APC, an important tumor suppressor. Hence, being infected with any of the TTV's encoding for the miRNA's included in the present invention could represent a risk factor for the development of colon cancer, as well as many other cancer types.

To support these findings, the inventors detected TTV miRNA's that down-regulate APC in a higher frequency in colon adenocarcinoma patients in comparison to other three types of cancer (lung adenocarcinoma, hepatocellular carcinoma and breast invasive carcinoma). Consequently, TTV miRNA's presented here represent a target for the prevention of colon cancer, as well as a putative biomarker for the early detection of a subset of these cancers.

REFERENCES

1. Nishizawa, T., Okamoto, H., Konishi, K., Yoshizawa, H., Miyakawa, Y.& Mayumi, M. (1997). A novel DNA virus (TTV) associated with elevated transaminase levels in posttransfusion hepatitis of unknown etiology. Biochem Biophys Res Commun 241, 92-97.
2. Okamoto, H., Nishizawa, T., Kato, N., Ukita, M., Ikeda, H., Iizuka, H., Miyakawa, Y. & Mayumi, M. (1998). Molecular cloning and characterization of a novel DNA virus (TTV) associated with posttransfusion hepatitis of unknown etiology. Hepatol Res 10, 1-16.
3. Miyata, H., Tsunoda, H., Kazi, A., Yamada, A., Khan, M. A., Murakami, J., Kamahora, T., Shiraki, K. & Hino, S. (1999). Identification of a novel GC-rich 113-nucleotide region to complete the circular, singlestranded DNA genome of TT virus, the first human circovirus. J Virol 73, 3582-3586.
4. Suzuki T, Suzuki R, Li J, Hijikata M, Matsuda M, Li T C, Matsuura Y, Mishiro S, Miyamura T (2004) Identification of basal promoter and enhancer elements in an untranslated region of the TT virus genome. J Virol 78: 10820-10824
5. Sébastien Pfeffer, Mihaela Zavolan, Friedrich A. Grasser, Minchen Chien, James J. Russo, Jingyue Ju, Bino John, Anton J. Enright, Debora Marks, Chris Sander, and Thomas Tuschl (2004) Identification of Virus-Encoded MicroRNAs Science 304 (5671), 734. [DOI: 10.1126/science.10 96781]
6. Aleksandra Helwak, Grzegorz Kudla, Tatiana Dudnakova, David Tollervey (2013) Mapping the Human miRNA Interactome by CLASH Reveals Frequent Noncanonical Binding. Cell 153, Issue 3, 654-665, ISSN 0092-8674
7. Lewis B P, Shih I H, Jones-Rhoades M W, Bartel D P, Burge C B (2003) Prediction of mammalian microRNA targets. Cell 115: 787-798.
8. J. Brennecke, A. Stark, R. B. Russell, S. M. Cohen(2005) Principles of microRNA-target recognition PLoS Biol., 3, p. e85
9. Meister, G. et al (2004) Human Argonaute2 mediates RNA cleavage targeted by miRNAs and siRNAs. Mol. Cell 15, 185-197
10. Pillai, R. S., Artus, C. G. & Filipowicz, W (2004) Tethering of human Ago proteins to mRNA mimics the miRNA-mediated repression of protein synthesis. RNA 10, 1518-1525
11. Eulalio, A., Huntzinger, E. & Izaurralde, E (2008) Getting to the root of miRNA-mediated gene silencing. Cell 132, 9-14.
12. Filipowicz, W., Bhattacharyya, S. N. & Sonenberg, N (2008) Mechanisms of post-transcriptional regulation by microRNAs: are the answers in sight? Nature Rev. Genet. 9, 102-114
13. Kozomara A, Griffiths-Jones S (2011) miRBase: integrating microRNA annotation and deep-sequencing data. Kozomara A, Griffiths-Jones S. N 2011 39(Database Issue):D152-D157

14. Griffiths-Jones S, Saini H K, van Dongen S, Enright A J. (2008) miRBase: tools for microRNA genomics. Nucleic Acids Res 36 (Database Issue):D154-D158
15. Griffiths-Jones S, Grocock R J, van Dongen S, Bateman A, Enright A J. (2006) miRBase: microRNA sequences, targets and gene nomenclature. Nucleic Acids Res 34 (Database Issue):D140-D144
16. The microRNA Registry.Griffiths-Jones S. (2004) Nucleic Acids Res 32(Database Issue):D109-D111
17. Sullivan C S, Grundhoff A T, Tevethia S, Pipas J M, Ganem D (2005) SV40-encoded microRNAs regulate viral gene expression and reduce susceptibility to cytotoxic T cells. Nature 435:682-86
18. Cullen, B. R. (2013). MicroRNAs as mediators of viral evasion of the immune system. Nature Immunology, 14(3), 205-210.
19. Bauman, Y., Nachmani, D., Vitenshtein, A., Tsukerman, P., Drayman, N., Stern-Ginossar, N., . . . & Mandelboim, O. (2011). An identical miRNA of the human JC and BK polyoma viruses targets the stress-induced ligand ULBP3 to escape immune elimination. Cell host & microbe, 9(2), 93-102
20. Vereide, D. T., Seto, E., Chiu, Y. F., Hayes, M., Tagawa, T., Grundhoff, A., . . . & Sugden, B. (2013). Epstein-Barr virus maintains lymphomas via its miRNAs. Oncogene.
21. Okamoto, H., T. Nishizawa, M. Takahashi, S. Asabe, F. Tsuda, and A. Yoshikawa (2001) Heterogeneous distribution of TT virus of distinct genotypes in multiple tissues from infected humans. Virology 288:358-368.
22. I. K. Mushahwar, J. C. Erker, A. S. Muerhoff, T. P. Leary, J. N. Simons, L. G. Birkenmeyer, M. L. Chalmers, T. J. Pilot-Matias, S. M. Desai (1999) Molecular and biophysical characterization of TT virus: Evidence for a new virus family infecting humans. Proc. Natl. Acad. Sci. 96: 3177-3182.
23. Irving, W. L., J. K. Ball, S. Berridge, R. Curran, A. M. Grabowska, C. L. Jameson, K. R. Neal, S. D. Ryder, and B. J. Thomson (1999) TT virus infection in patients with hepatitis C: frequency, persistence and sequence heterogeneity. J. Infect. Dis. 180:27-34.
24. de Villiers E M, Borkosky S S, Kimmel R, Gunst K, Fei J W (2011) The diversity of torque teno viruses: in vitro replication leads to the formation of additional replication-competent subviral molecules. J. Virol. 85:7284-7295.
25. Jelcic I, Hotz-Wagenblatt A, Hunziker A, Zur Hausen H, de Villiers E M (2004) Isolation of multiple TT virus genotypes from spleen biopsy tissue from a Hodgkin's disease patient: genome reorganization and diversity in the hypervariable region. J. Virol. 78:7498-7507.
26. Leppik L., Gunst K., Lehtinen M., Dillner J., Streker K., de Villiers E. M. (2007) In vivo and in vitro intragenomic rearrangement of TT viruses. J Virol 81, 9346-9356.
27. Ninomiya, M., et al (2007) Identification and genomic characterization of a novel human torque teno virus of 3.2 kb. J. Gen. Virol. 88:1939-1944.
28. Ninomiya, M., M. Takahashi, T. Nishizawa, T. Shimosegawa, and H. Okamoto (2008) Development of PCR assays with nested primers specific for differential detection of three human anelloviruses and early acquisition of dual or triple infection during infancy. J. Clin. Microbiol. 46:507-514.
29. Kim, D. H., Sætrom, Snøve, O., & Rossi, J. J. (2008). MicroRNA-directed transcriptional gene silencing in mammalian cells. Proceedings of the National Academy of Sciences, 105(42), 16230-16235.
30. Sepramaniam, S., Armugam, A., Wintour, E. M., & Jeyaseelan, K (2012). MicroRNA-130a Represses Transcriptional Activity of Aquaporin 4 Ml Promoter. Journal of Biological Chemistry, 287(15), 12006-12015.
31. Younger S T, Corey D R (2011) Transcriptional gene silencing in mammalian cells by miRNA mimics that target gene promoters. Nucleic Acids Res; 39:5682-91
32. Huang V, Place R F, Portnoy V, Wang J, Q Z., Jia Z, et al. Upregulation of Cyclin B1 by miRNA and its implications in cancer. Nucleic Acid Res 2011
33. Place R F, Li L C, Pookot D, Noonan E J, Dahiya R. MicroRNA-373 induces expression of genes with complementary promoter sequences. Proc Natl Acad
34. Tyaqi, S., Vaz, C., Gupta, V. Bhatia, R., Maheshwari, Srinivasan, A., & Bhattacharya, A. (2008). CID-miRNA: a web server for prediction of novel miRNA: precursors in human genome. Biochemical and biophysical research communications, 372(4), 831-834.
35. Grundhoff, A. (2011). Computational prediction of viral miRNAs. In Antiviral RNAi (pp. 143-152). Humana Press.
36. Grundhoff, A., Sullivan, C. & Ganem, D. (2006). A combined computational and microarray-based approach identifies novel microRNAs encoded by human gammaherpesviruses. Rna, 12(5), 733-750.
37. Gkirtzou, K., Tsamardinos, I., Tsakalides, P., & Poirazi, P. (2010). MatureBayes: a probabilistic algorithm for identifying the mature miRNA within novel precursors. PloS one, 5(8), e11843.
38. M. Maragkakis; P. Alexiou; G. L. Papadopoulos; M. Reczko; T. Dalamagas; G. Giannopoulos; Goumas; E. Koukis; K. Kourtis; V. A. Simossis; P. Sethupathy; T. Vergoulis; N. Koziris; T. Sellis; P. Tsanakas; A. G. Hatzigeorgiou. Accurate microRNA target prediction correlates with protein repression levels. BMC Bioinformatics 2009, 10:295
39.2/ M. Maragkakis; Reczko; V. A. Simossis; P. Alexiou; G. L. Papadopoulos; T. Dalamagas; G. Giannopoulos; G. Goumas; E. Koukis; K. Kourtis; T. Vergoulis; N. Koziris; T. Sellis; P. Tsanakas; A. G. Hatzigeorgiou. DIANA-microT web server: elucidating microRNA functions though target prediction. Nucleic Acids Research. 2009 Jul. 1; 37(Web Server issue):W273-6
40. Rehmsmeier, M., Steffen, P., Höchsmann, M., & Giegerich, R. (2004). Fast and effective prediction of microRNA/target duplexes. Rna, 10 (10), 1507-1517
41. Borkosky, S. S., Whitley, C., Kopp-Schneider, A., & Zur Hausen, H. (2012). Epstein-Barr Virus Stimulates Torque Teno Virus Replication: A Possible Relationship to Multiple Sclerosis. PloS one, 7(2), e32160
42. Mariscal, L. F., López-Aicorocho, J. M., Rodriguez-Iñigo, E., Ortiz-Movilla, N., de Lucas, S., Bartolomë, J., Carreño, (2002). TT virus replicates in stimulated but not in nonstimulated peripheral blood mononuclear cells. Virology, 301(1), 121-129.
43. Bur Hausen, H., & de Villiers, P. M. (2009). TT viruses: oncogenic or tumor-suppressive properties?. In Ti Viruses (pp. 109-116). Springer Berlin Heidelberg.
44. hong, S., Yeo, W., Tang, M. W., LIN, K. R., Mo, F., Ho, W. M. & Johnson, P. J. (2001). Gross elevation of TT virus genome load in the peripheral blood mononuclear cells of cancer patients. Annals of the New York Academy of Sciences, 945 (1), 84-92.
45. Madsen, C. D., Eugen-Olsen, J., Kirk, O., Darner, J., Christensen, J. K., Brasholt, M. S., & Krogsgaard, K. (2002). TTV viral load as a marker for immune reconstitution after initiation of HAART in HIV-infected patients. HIV Clinical Trials, 3 (4), 287-295
46. Thom, K., & Petrick, J. (2007). Progression towards AIDS leads to increased Torque teno virus and Torque teno minivirus titers in tissues of HIV infected individuals. Journal of medical virology, 79 (1), 1-7
47. Van Es, H., Kirkpatrick, C., Van de Wetering, M., Molenaar, M., Miles, A., Kuipers, J., & Clevers, H. (1999) Identification of APC2, a homologue of the adenomatous polyposis coli tumour suppressor. Current biology, 9 (2), 105-S2
48. Nakagawa, H., Murata, Y., Koyama, K., Fujiyama, A., Miyoshi, Monden, N., & Nakamura, Y. (1998) Identification of a brain-specific APC homologue, APCL, and its interaction with ß-catenin. Cancer research, 58 (22), 5176-5181.
49. Mokarram, P., Kumar, K., Brim, H., Naghibalhossaini, F., Saberi-Firoozi, M., Nouraie, M., & Ashktorab H (2009) Distinct high-profile methylated genes in colorectal cancer. PLoS One, 4(9), e7012.
50. Chen, H. J., Lin, C. M., Din, C. S., Perez-Olle, R., Leung, C. L., & Diem, R. K. (2006). The role of microtubule actin cross-linking factor 1 (MACF1) in the Nut signaling pathway. Genes & development, 20(14), 1933-1945.
51. Suozzi, K. C., Wu, X., & Fuchs, E. (2012). Spectrapiakins: Master orchestrators of cytoskeletal dynamics. The Journal of cell biology, 197(4), 465-475.
52. Zaoui, K., Benseddik, K., Daou, P., Salaün, D., & Badache, (2010). ErbB2 receptor controls microtubule capture by recruiting ACF7 to the plasma membrane of migrating cells. Proceedings of the National Academy of Sciences, 107(43), 18517-18522.
53. Aaltonen, L. A., Peltomaki, P., Leach, F. S., Sistonen, P., Pylkkanen, L., Mecklin, J. P., & Jen, J. (1993). Clues to the pathogenesis of colorectal cancer. Science, 260(5109), 812-816
54. Dreos, R., Ambrosini, G., Périer, R. C., & Bucher, P. (2013). EPD and EPDnew, high-quality promoter resources in the next-generation sequencing era. Nucleic acids research, 41(D1), 0157-D164.
55. Munemitsu, S., Albert, I., Souza, B., Rubinfeld, B., & Polakis, P. (1995). Regulation of intracellular beta-catenin levels by the *adenomatous polyposis coli* (APC) tumor suppressor protein. Proceedings of the National Academy of Sciences, 92 (7), 3046-3050.
56. Grace, A., Butler, D., Gallagher, M., Al-Agha, R., Kin, Y., Leader, M., & Kay, F. (2002). APC gene expression in gastric carcinoma: an immunohistochemical study. Applied Immunohistochemistry & Molecular Morphology, 10(3), 221-224.
57. Perez-Sayáns, M., Suárez-Peñaranda, J. M., Herranz-Carnero, M., Gayoso-Diz, P., Barros-Angueira, F., Gándara-Rey, J. M., & Garcia-Garcia, A. (2012). The role of the *adenomatous polyposis coli* (APC) in oral squamous cell carcinoma. Oral oncology, 48(1), 56-60.
58. Lee, H. C., Kim, M., & Wands, J. R. (2006). Wnt/Frizzled signaling in hepatocellular carcinoma. Front Biosci, 11(5), 1901-115.
59. Reya, T., & Clevers, H. (2005) Wnt signalling in stem cells and cancer. Nature, 434 (7035), 843-850.
60. Fodde, R., Smits, R., & Clevers, H. (2001). APC, signal transduction and genetic instability in colorectal cancer. Nature Reviews Cancer, 1(1), 55-67.
61. Klaus, A., & Birchmeier, W. (2008). Writ signalling and its impact on development and cancer. Nature Reviews Cancer, 8(5), 387-398,
62. Chen, J., Röcken, C., Lofton-Day, C., Schulz, H. U., O., Kutzner, N., . . . & Ebert, M. P. (2005). Molecular analysis of APC promoter methylation and protein expression in colorectal cancer metastasis. Carcinogenesis, 26(1), 37-43.
63. Esteller, M., Sparks, A., Toyota, Sanchez-Cespedes, M., Capella, G., Peinado, Herman, J. G. (2000). Analysis of *adenomatous polyposis coli* promoter hypermethylation in human cancer. Cancer research, 60(16), 4366-4371.
64. Arnold, C. N., Goel, Niedzwiecki, D., Dowell, J. M., Wasserman, L., Compton, C., . . . & Boland, C. R. (2004). APC promoter hypermethylation contributes to the loss of APC expression in colorectal cancers with allelic loss on 5 ql. Cancer biology & therapy, 3(10), 960-964.
65. Samowitz, W. S., Slattery, M. L., Sweeney, C., Herrick, J., Wolff, R. K., & Albertsen, H. (2007). APC mutations and other genetic and epigenetic changes in colon cancer. Molecular cancer research, 5 (2), 165-170.
66. Nagel, R., le Sage, C., Diosdado, B., van der Waal, M., Vrielink, J. A., O., Bolijn, A., . . . & Agami, R. (2008). Regulation of the *adenomatous polyposis coli* gene by the miR-135 family in colorectal cancer. Cancer Research, 68(14), 5795-5802.
67. Karreth, A., Tay, Y., Perna, D., Ala, U., Tan, S. M., Rust, A. G., & Pandolfi, P. P. (2011). In vivo identification of tumor-suppressive PTEN ceRNAs in an oncogenic BRAF-induced mouse model of melanoma. Cell, 147 (2), 382-395.
68. Liu, P, Ramachandra, S., Seyed, M. A., Scharer, D., Laycock, N., Dalton, W. B., & Moreno, C. S. (2006). Sex-determining region Y box 4 is a transforming oncogene in human prostate cancer cells. Cancer research, 66(8), 4011-4019.
69. Bagchi, A., Papazoglu, C., Wu, Y., Capurso, D., Brodt, M., Francis, D., . . . & Mills, A. A. (2007) CHD5 is a Tumor Suppressor at Human 1p36. Cell, 1283), 459-475.
70. Deshmukh, Yu, J., Shaik, J., MacDonald, T., Perry, A., Payton, J., & Nagarajan, R. (2011). Identification of transcriptional regulatory networks specific to pilocytic astrocytoma. BMC medical genomics, 4(1), 57.
71. Botchkina, I. L., Rowehl, R. A., rivadeneira, D. E., karpeh, M. S., crawford, H., dufour, A., & botchkina, G. I. (2009). Phenotypic subpopulations of metastatic colon cancer stem cells: genomic analysis. Cancer Genomics-Proteomics, 6(1), 19-29.
72. Revillion, F., Pawlowski, V., Hornez, L., & Peyrat, J. P. (2000). Glyceraldehyde-3-phosphate dehydrogenase gene expression in human breast cancer. *European Journal of Cancer*, 36(8), 1038-1042.
73. Tokunaga, K., Nakamura, Y., Sakata, K., Fujimori, K., Ohkubo, M., Sawada, K., & Sakiyama, S. (1987). Enhanced expression of a glyceraldehyde-3-phosphate dehydrogenase gene in human lung cancers. *Cancer research*, 47(21), 5616-5619.
74. Majmundar, A. J., Wong, W. J., & Simon, M. C. (2010). Hypoxia-inducible factors and the response to hypoxic stress. *Molecular cell*, 40(2), 294-309.
75. Semenzax, G. L. (2003). Targeting HIF-1 for cancer therapy. *Nature Reviews Cancer*, 3(10), 721-732.
76. Buck, C. B., Thompson, C. D., Pang, Y. Y., Lowy, D. r., Schiller J. T. (2005) Maturation of papillomavirus capsids. J Virology 79(5), 2839-2846.
77. Okamoto H., (2009). TT viruses in animals. Curr Top Microbiol Immunol 331:35-52.
78. Kincaid, R. P., Burke, J. M., Cox, J. M., De Villiers, E. M., Sullivan C. S. (2013) A human Torque Teno virus encodes a miRNA that inhibits interferon signalling. PLoS Pathog 9(12): e1003818. doi:10.1371/journal.ppat.1003818
79. Valeri N., et Al. (2014) MicroRNA-135b Promotes Cancer Progression by Acting as a Downstream Effector of Oncogenic Pathways in Colon Cancer. Cancer Cell, Volume 25, Issue 4, 469-483
80. Farh K. K-H., et Al. (2005) The Widespread Impact of Mammalian MicroRNAs on mRNA Repression and Evolution. Science, Vol. 310 no. 5755, 1817-1821.
81. Stenvang, J., et al., Inhibition of microRNA function by antimiR oligonucleotides. Silence, 2012. 3(1): p. 1.
82. Haraguchi, T., Y. Ozaki, and H. Iba, *Vectors expressing efficient RNA decoys achieve the long-term suppression of specific microRNA activity in mammalian cells*. Nucleic acids research, 2009: p. gkp040.
83. Bak, R. O., et al., *Potent microRNA suppression by RNA Pol II-transcribed 'Tough Decoy' inhibitors*. RNA, 2013. 19(2): p. 280-293.
84. Mingozzi, F. and K. A. High, *Therapeutic in vivo gene transfer for genetic disease using AAV: progress and challenges*. Nature reviews genetics, 2011. 12(5): p. 341-355.
85. Cheng, C. J., et al., *MicroRNA silencing for cancer therapy targeted to the tumour microenvironment*. Nature, 2014.
86. Mitchell, P. S., et al., *Circulating microRNAs as stable blood-based markers for cancer detection*. Proceedings of the National Academy of Sciences, 2008. 105(30): p. 10513-10518.

The invention claimed is:

1. A vector comprising a TTV nucleic acid operatively linked to a promoter, wherein the TTV nucleic acid consists of a nucleotide sequence selected from the group consisting of SEQ ID NOs: 1-4, 12, and 38-55.

2. A labeled primer comprising a label and an oligonucleotide of at least 15 nucleotides, wherein the oligonucleotide is comprised by a sequence selected from the group consisting of SEQ ID NOs: 38-44, 46-55, wherein the oligonucleotide comprises the nucleotide sequence CATCCYY (with Y=C or T).

3. The primer of claim 2, wherein the nucleotide sequence CATCCYY is selected from the group consisting of CATCCCC, CATCCCT, and CATCCTC.

* * * * *

SEQUENCE LISTING

```
<160> NUMBER OF SEQ ID NOS: 94

<210> SEQ ID NO 1
<211> LENGTH: 69
<212> TYPE: RNA
<213> ORGANISM: torque teno virus

<400> SEQUENCE: 1
gccucggacc cccccucgac cagaaucgcu cgcgcgauuc ggaccugcgg ccucgggggg      60
gucggggc                                                              69

<210> SEQ ID NO 2
<211> LENGTH: 78
<212> TYPE: RNA
<213> ORGANISM: torque teno virus

<400> SEQUENCE: 2
gcugugacgu caacgucacg uggggaggac ggcguguaac ccggaaguca ucccccaucac     60 gugaccugac gucacggc                                                   78

<210> SEQ ID NO 3
<211> LENGTH: 63
<212> TYPE: RNA
<213> ORGANISM: torque teno virus

<400> SEQUENCE: 3
ccgccgcuac gucacacuuc cucuuuuuuu uacaaaaagc ggaaggaagu cacaagaugg      60
cgg                                                                   63

<210> SEQ ID NO 4
<211> LENGTH: 80
<212> TYPE: RNA
<213> ORGANISM: torque teno virus

<400> SEQUENCE: 4
ggccgugacg ucaggucacg ugauggggau gacuuccggg uuacacgccg uccucccccac    60 gugacguuga cgucacagcc                                                 80

<210> SEQ ID NO 5
<211> LENGTH: 86
<212> TYPE: DNA
<213> ORGANISM: torque teno virus

<400> SEQUENCE: 5
ggccgccatt ttaagtaagg cggaagcaac tccactttct cacaaaatgg cggcggagca     60
```

```
cttccggctt gcccaaaatg gccgcc                                              86

<210> SEQ ID NO 6
<211> LENGTH: 82
<212> TYPE: DNA
<213> ORGANISM: torque teno virus

<400> SEQUENCE: 6
ccgccatttt aagtaaggcg gaagcagctc cactttctca caaaatggcg gcggagcact        60
tccggcttgc ccaaaatggc gg                                                 82

<210> SEQ ID NO 7
<211> LENGTH: 82
<212> TYPE: DNA
<213> ORGANISM: torque teno virus

<400> SEQUENCE: 7
ccgccatttt aagtaaggcg gaagcagctc caccctctca cataatggcg gcggagcact        60
cccggcttgc ccaaaatggc gg                                                 82

<210> SEQ ID NO 8
<211> LENGTH: 82
<212> TYPE: DNA
<213> ORGANISM: torque teno virus

<400> SEQUENCE: 8
gccgccattt taagtaaggc ggaagcagct cggcatatac aaaatgtcgg cggagcactt        60
ccggcttacc caaaatgaag gc                                                 82

<210> SEQ ID NO 9
<211> LENGTH: 69
<212> TYPE: DNA
<213> ORGANISM: torque teno virus

<400> SEQUENCE: 9
gcctcggacc cccctcgac cagaatcgct cgcgcgattc ggacctgcgg cctcgggggg         60
gtcggggc                                                                 69

<210> SEQ ID NO 10
<211> LENGTH: 67
<212> TYPE: DNA
<213> ORGANISM: torque teno virus

<400> SEQUENCE: 10
cctcggaccc ccccccgacc cgaatcgctc gcgcgattcg gacctgcggc ctcgggggg         60 gtcgggg                                                                  67

<210> SEQ ID NO 11
<211> LENGTH: 61
<212> TYPE: DNA
<213> ORGANISM: torque teno virus

<400> SEQUENCE: 11
cctcggaccc ccgctcgtgc tgacgcgctt gcgcgcgtca gaccacttcg ggctcgcggg        60
g                                                                        61

<210> SEQ ID NO 12
<211> LENGTH: 78
<212> TYPE: DNA
```

```
<213> ORGANISM: torque teno virus

<400> SEQUENCE: 12
gctgtgacgt caacgtcacg tggggaggac ggcgtgtaac ccggaagtca tccccatcac    60
gtgacctgac gtcacggc                                                  78

<210> SEQ ID NO 13
<211> LENGTH: 70
<212> TYPE: DNA
<213> ORGANISM: torque teno virus

<400> SEQUENCE: 13
acgtcacaag tcacgtgggg agggttggcg tatagcccgg aagtcaatcc tcccacgtgg    60
cctgtcacgt                                                           70

<210> SEQ ID NO 14
<211> LENGTH: 83
<212> TYPE: DNA
<213> ORGANISM: torque teno virus

<400> SEQUENCE: 14
gcagctacgt cacaagtcac ctgactgggg aggagttaca tcccggaagt tctcctcggt    60
cacgtgactg tacacgtgac tgc                                            83

<210> SEQ ID NO 15
<211> LENGTH: 71
<212> TYPE: DNA
<213> ORGANISM: torque teno virus

<400> SEQUENCE: 15
acgtcacaag tcacctgact ggggaggagt cacaacccgg aagtcctctt cggtcacgtg    60
actagtcacg t                                                         71

<210> SEQ ID NO 16
<211> LENGTH: 80
<212> TYPE: DNA
<213> ORGANISM: torque teno virus

<400> SEQUENCE: 16
ggccgtgacg tcaggtcacg tgatggggat gacttccggg ttacacgccg tcctccccac    60
gtgacgttga cgtcacagcc                                                80

<210> SEQ ID NO 17
<211> LENGTH: 75
<212> TYPE: DNA
<213> ORGANISM: torque teno virus

<400> SEQUENCE: 17
cgtgacgtca gagtcacgtg accagggatg cttccgggtt taggcacgcc cccatcacgt    60
gtctcaaacg tcacg                                                     75

<210> SEQ ID NO 18
<211> LENGTH: 83
<212> TYPE: DNA
<213> ORGANISM: torque teno virus

<400> SEQUENCE: 18
gcagtcacgt gtacagtcac gtgaccgagg agaacttccg ggatgtaact cctccccagt    60
caggtgactt gtgacgtagc tgc                                            83
```

<210> SEQ ID NO 19
<211> LENGTH: 71
<212> TYPE: DNA
<213> ORGANISM: torque teno virus

<400> SEQUENCE: 19
acgtgactag tcacgtgacc gaagaggact tccgggttgt gactcctccc cagtcaggtg    60
acttgtgacg t    71

<210> SEQ ID NO 20
<211> LENGTH: 70
<212> TYPE: DNA
<213> ORGANISM: torque teno virus

<400> SEQUENCE: 20
acgtgaccag ttacgtggtt gaggatactt cagtgtttaa gtacctcccc agtcacgtga    60
cttatgacgt    70

<210> SEQ ID NO 21
<211> LENGTH: 78
<212> TYPE: DNA
<213> ORGANISM: torque teno virus

<400> SEQUENCE: 21
gccattttgg gcaagccgga agtgctccgc cgccattttg tgagaaagtg gagttgcttc    60
cgccttactt aaaatggc    78

<210> SEQ ID NO 22
<211> LENGTH: 82
<212> TYPE: DNA
<213> ORGANISM: torque teno virus

<400> SEQUENCE: 22
ccgccatttt gggcaagccg gaagtgctcc gccgccattt tgtgagaaag tggagctgct    60
tccgccttac ttaaaatggc gg    82

<210> SEQ ID NO 23
<211> LENGTH: 82
<212> TYPE: DNA
<213> ORGANISM: torque teno virus

<400> SEQUENCE: 23
ccgccatttt gggcaagccg ggagtgctcc gccgccatta tgtgagaggg tggagctgct    60
tccgccttac ttaaaatggc gg    82

<210> SEQ ID NO 24
<211> LENGTH: 82
<212> TYPE: DNA
<213> ORGANISM: torque teno virus

<400> SEQUENCE: 24
gccttcattt tgggtaagcc ggaagtgctc cgccgacatt ttgtatatgc cgagctgctt    60
ccgccttact taaatggcg gc    82

<210> SEQ ID NO 25
<211> LENGTH: 72
<212> TYPE: DNA
<213> ORGANISM: torque teno virus

<400> SEQUENCE: 25 ccatttttgag taggtgtggc tgatggtgac ctttgaactc acgccaccgt ccgcctcaac    60
tacttaagat gg    72

<210> SEQ ID NO 26
<211> LENGTH: 73
<212> TYPE: DNA
<213> ORGANISM: torque teno virus

<400> SEQUENCE: 26 ccatttttgtg tagcttccgt cgaggatgac ctttaacctc tacgtcaatc ctgacgtcag    60
ctacttaaaa tgg    73

<210> SEQ ID NO 27
<211> LENGTH: 63
<212> TYPE: DNA
<213> ORGANISM: torque teno virus

<400> SEQUENCE: 27
ccgccgctac gtcacacttc ctcttttttt tacaaaaagc ggaaggaagt cacaagatgg    60
cgg    63

<210> SEQ ID NO 28
<211> LENGTH: 64
<212> TYPE: DNA
<213> ORGANISM: torque teno virus

<400> SEQUENCE: 28
ccgccgctac tgtcatactt cctctttttt tttgaaaaag cggaaggaag tcacaagatg    60
gcgg    64

<210> SEQ ID NO 29
<211> LENGTH: 68
<212> TYPE: DNA
<213> ORGANISM: torque teno virus

<400> SEQUENCE: 29 gccgggggggc tgccgccccc cccggggaaa ggggggggcc cccccgggg ggggtttgc    60 ccccggc    68

<210> SEQ ID NO 30
<211> LENGTH: 79
<212> TYPE: DNA
<213> ORGANISM: torque teno virus

<400> SEQUENCE: 30
gtcgtgacgt ttgagacacg tgatgggggc gtgcctaaac ccggaagcat ccctggtcac    60
gtgactctga cgtcacggc    79

<210> SEQ ID NO 31
<211> LENGTH: 62
<212> TYPE: DNA
<213> ORGANISM: torque teno virus

<400> SEQUENCE: 31 gcggggggggc ggccgcgttc gcgcgccgcc caccaggggg tgctgcgcgc ccccccccgc    60
gc    62

<210> SEQ ID NO 32
<211> LENGTH: 69
<212> TYPE: DNA
<213> ORGANISM: torque teno virus

<400> SEQUENCE: 32
gtgcctacct cttaaggtca ccaagcactc cgagcgtcag cgaggagtgc gacccttggg    60
ggtgggtgc                                                            69

<210> SEQ ID NO 33
<211> LENGTH: 86
<212> TYPE: DNA
<213> ORGANISM: torque teno virus

<400> SEQUENCE: 33
ggccgccatt ttaagtaagg cggaagcaac tccactttct cacaaaatgg cggcggagca    60
cttccggctt gcccaaaatg gccgcc                                          86

<210> SEQ ID NO 34
<211> LENGTH: 68
<212> TYPE: DNA
<213> ORGANISM: torque teno virus

<400> SEQUENCE: 34 gccgggggc aaaccccccc ccggggggggg cccccccctt tccccggggg gggcggcagc    60
cccccggc                                                              68

<210> SEQ ID NO 35
<211> LENGTH: 72
<212> TYPE: DNA
<213> ORGANISM: torque teno virus

<400> SEQUENCE: 35
ccagaaggcg gcggcctcgt actcctgctg ccagtcttgg ctgctgggta cgggttttgg    60
ggccctgtct gg                                                        72

<210> SEQ ID NO 36
<211> LENGTH: 79
<212> TYPE: DNA
<213> ORGANISM: torque teno virus

<400> SEQUENCE: 36
cgcgcatgcg cggtgggttt agcacggggg ggggccgggg gggcggagcc ccccgggggg    60
ggggccccgc gcatgcgcg                                                 79

<210> SEQ ID NO 37
<211> LENGTH: 64
<212> TYPE: DNA
<213> ORGANISM: torque teno virus

<400> SEQUENCE: 37 gggggtccg aggcgtccgg cgcagcgcga agcgcgtagc gccggacccc gaggaagttg     60
cccc                                                                 64

<210> SEQ ID NO 38
<211> LENGTH: 79
<212> TYPE: DNA
<213> ORGANISM: torque teno virus

<400> SEQUENCE: 38

```
gctgtgacgt atcagtcacg tgggaagggt gtgccttaac ccggaagcat ccctggtcac    60
gtgactgtga cgtcgcggc                                                 79

<210> SEQ ID NO 39
<211> LENGTH: 79
<212> TYPE: DNA
<213> ORGANISM: torque teno virus

<400> SEQUENCE: 39
gctgtgacgt atcagtcacg tgggaagggc gtgccttaac ccggaagcat ccctggtcac    60
gtgactgtga cgtcgcggc                                                 79

<210> SEQ ID NO 40
<211> LENGTH: 79
<212> TYPE: DNA
<213> ORGANISM: torque teno virus

<400> SEQUENCE: 40
gctgtgacgt ttaagtcacg tgggcgggc gtgccttaac ccggaagcat ccctggtcac     60
gtgactgtga cgtcgcggc                                                 79

<210> SEQ ID NO 41
<211> LENGTH: 79
<212> TYPE: DNA
<213> ORGANISM: torque teno virus

<400> SEQUENCE: 41
gtcgtgacgt ttgagacacg tgattggggc gtgcctaaac ccggaagcat ccctggtcac    60
gtgactctga cgccacggc                                                 79

<210> SEQ ID NO 42
<211> LENGTH: 79
<212> TYPE: DNA
<213> ORGANISM: torque teno virus

<400> SEQUENCE: 42
gtcgtgacgt ttgagacacg tgattggggc gtgcctaaac ccggaagcat ccctggtcac    60
gtgactctga cgccacggc                                                 79

<210> SEQ ID NO 43
<211> LENGTH: 85
<212> TYPE: DNA
<213> ORGANISM: torque teno virus

<400> SEQUENCE: 43
tcatctatac gtcataagtc acgtgggaag gggtgtgccc ttaaacccgg aagcatcctc    60
gtccacgtga ctgtgacgtg tatga                                          85

<210> SEQ ID NO 44
<211> LENGTH: 85
<212> TYPE: DNA
<213> ORGANISM: torque teno virus

<400> SEQUENCE: 44
tcatgtgtac gtcataagtc acgtgagaag gggcgtgcct ttaaattcgg aagcatcctc    60
gtccacgtga ctgtgacgtg tatga                                          85

<210> SEQ ID NO 45
<211> LENGTH: 78
```

```
<212> TYPE: DNA
<213> ORGANISM: torque teno virus

<400> SEQUENCE: 45
gctgtgacgt caacgtcacg tggggaggac ggcgtgtaac ccggaagtca tcctcatcac    60
gtgacctgac gtcacggc                                                  78

<210> SEQ ID NO 46
<211> LENGTH: 76
<212> TYPE: DNA
<213> ORGANISM: torque teno virus

<400> SEQUENCE: 46 ccatttttaag taagctccac ccaggactga cgtcagtgtg aaaggtcatc ctcggcggga   60
acttacatga aatggc                                                    76

<210> SEQ ID NO 47
<211> LENGTH: 76
<212> TYPE: DNA
<213> ORGANISM: torque teno virus

<400> SEQUENCE: 47
ccattttaag taggtgtcgt ccaggactgc tgttccgggt caggggggcat cctcggcgga   60 acttacacaa aatggc                                                    76

<210> SEQ ID NO 48
<211> LENGTH: 76
<212> TYPE: DNA
<213> ORGANISM: torque teno virus

<400> SEQUENCE: 48
ccattttaag taggtgccgt ccaggactgc tgttccgggt cagacggcat cctcggcgga    60
acttacacaa aatggc                                                    76

<210> SEQ ID NO 49
<211> LENGTH: 76
<212> TYPE: DNA
<213> ORGANISM: torque teno virus

<400> SEQUENCE: 49
ccattttgag taggtgccgt ccaggactcc tgttccgggt cagagggcat cctcggcgga    60
acttacacaa aatggc                                                    76

<210> SEQ ID NO 50
<211> LENGTH: 76
<212> TYPE: DNA
<213> ORGANISM: torque teno virus

<400> SEQUENCE: 50
ccattttaag taggtgccgt ccaggactgc tgttccgggt cagagggcat cctcggcgga    60
acctgcacaa aatggt                                                    76

<210> SEQ ID NO 51
<211> LENGTH: 77
<212> TYPE: DNA
<213> ORGANISM: torque teno virus

<400> SEQUENCE: 51
ccattttaag taggtgccgt ccaggactgc tgttccgggt cagagggcat cctcggcgga    60
```

```
acctacacaa aaatgga                                             77

<210> SEQ ID NO 52
<211> LENGTH: 75
<212> TYPE: DNA
<213> ORGANISM: torque teno virus

<400> SEQUENCE: 52
ccattttaag tcagcttcgg ggaggcatga cgtgtagttc aaaggtcatc ctcaccggaa    60
ctggcacaaa atggc                                                    75

<210> SEQ ID NO 53
<211> LENGTH: 75
<212> TYPE: DNA
<213> ORGANISM: torque teno virus

<400> SEQUENCE: 53
ccattttaag tcaacgctgg ggaggcgtga cgtacagttc aaaggtcatc ctcgccggaa    60
ctggcacaaa atggc                                                    75

<210> SEQ ID NO 54
<211> LENGTH: 75
<212> TYPE: DNA
<213> ORGANISM: torque teno virus

<400> SEQUENCE: 54
ccattttaag tcagcgctgg ggaggagtga cgtacagttc aaaggtcatc ctcgtcggaa    60
ctggcacaaa atggc                                                    75

<210> SEQ ID NO 55
<211> LENGTH: 77
<212> TYPE: DNA
<213> ORGANISM: torque teno virus

<400> SEQUENCE: 55
ccattttaag taagcaccgc ctaggactga cgtataagtt caaaggtcat cctcggccgg    60
aacttacaca aaatggt                                                  77

<210> SEQ ID NO 56
<211> LENGTH: 30
<212> TYPE: DNA
<213> ORGANISM: artificial sequence
<220> FEATURE:
<223> OTHER INFORMATION: probe

<400> SEQUENCE: 56
agcgattctg gtcgaggggg ggtccgaggc                                    30

<210> SEQ ID NO 57
<211> LENGTH: 37
<212> TYPE: DNA
<213> ORGANISM: artificial sequence
<220> FEATURE:
<223> OTHER INFORMATION: probe

<400> SEQUENCE: 57
gcccccgacc ccccgaggc cgcaggtccg aatcgcg                             37

<210> SEQ ID NO 58
<211> LENGTH: 37
<212> TYPE: DNA
<213> ORGANISM: artificial sequence
```

<220> FEATURE:
<223> OTHER INFORMATION: probe

<400> SEQUENCE: 58
acacgccgtc ctccccacgt gacgttgacg tcacagc                                37

<210> SEQ ID NO 59
<211> LENGTH: 37
<212> TYPE: DNA
<213> ORGANISM: artificial sequence
<220> FEATURE:
<223> OTHER INFORMATION: probe

<400> SEQUENCE: 59
gccgtgacgt caggtcacgt gatggggatg acttccg                                37

<210> SEQ ID NO 60
<211> LENGTH: 25
<212> TYPE: DNA
<213> ORGANISM: artificial sequence
<220> FEATURE:
<223> OTHER INFORMATION: probe

<400> SEQUENCE: 60
aagaggaagt gtgacgtagc ggcgg                                             25

<210> SEQ ID NO 61
<211> LENGTH: 26
<212> TYPE: DNA
<213> ORGANISM: artificial sequence
<220> FEATURE:
<223> OTHER INFORMATION: probe

<400> SEQUENCE: 61
cgccatcttg tgacttcctt ccgctt                                            26

<210> SEQ ID NO 62
<211> LENGTH: 36
<212> TYPE: DNA
<213> ORGANISM: artificial sequence
<220> FEATURE:
<223> OTHER INFORMATION: probe

<400> SEQUENCE: 62
cggaagtcat ccccatcacg tgacctgacg tcacgg                                 36

<210> SEQ ID NO 63
<211> LENGTH: 37
<212> TYPE: DNA
<213> ORGANISM: artificial sequence
<220> FEATURE:
<223> OTHER INFORMATION: probe

<400> SEQUENCE: 63
gctgtgacgt caacgtcacg tggggaggac ggcgtgt                                37

<210> SEQ ID NO 64
<211> LENGTH: 35
<212> TYPE: DNA
<213> ORGANISM: artificial sequence
<220> FEATURE:
<223> OTHER INFORMATION: probe

<400> SEQUENCE: 64
cactacctgc acgaacagca ctttggagcc cccag                                  35

```
<210> SEQ ID NO 65
<211> LENGTH: 35
<212> TYPE: DNA
<213> ORGANISM: artificial sequence
<220> FEATURE:
<223> OTHER INFORMATION: probe

<400> SEQUENCE: 65
ccgggggctc gggaagtgct agctcagcag taggt                             35

<210> SEQ ID NO 66
<211> LENGTH: 21
<212> TYPE: RNA
<213> ORGANISM: homo sapiens

<400> SEQUENCE: 66
uaguuuuaca ccgggggaug a                                            21

<210> SEQ ID NO 67
<211> LENGTH: 21
<212> TYPE: RNA
<213> ORGANISM: torque teno virus

<400> SEQUENCE: 67
ucucagugca cugguccucua c                                           21

<210> SEQ ID NO 68
<211> LENGTH: 24
<212> TYPE: RNA
<213> ORGANISM: homo sapiens

<400> SEQUENCE: 68
auguuaguuu uacaccgggg gaug                                         24

<210> SEQ ID NO 69
<211> LENGTH: 22
<212> TYPE: RNA
<213> ORGANISM: torque teno virus

<400> SEQUENCE: 69
acacauucaa ggcggcuccu ac                                           22

<210> SEQ ID NO 70
<211> LENGTH: 13
<212> TYPE: RNA
<213> ORGANISM: homo sapiens

<400> SEQUENCE: 70
agaucagagg gug                                                     13

<210> SEQ ID NO 71
<211> LENGTH: 21
<212> TYPE: RNA
<213> ORGANISM: torque teno virus

<400> SEQUENCE: 71
aguccagugc acuacuccua c                                            21

<210> SEQ ID NO 72
<211> LENGTH: 35
<212> TYPE: RNA
<213> ORGANISM: homo sapiens

<400> SEQUENCE: 72
```

-continued

```
aucagaauccaguagaaaag caaaaaguga ggaug                               35
```

<210> SEQ ID NO 73
<211> LENGTH: 21
<212> TYPE: RNA
<213> ORGANISM: torque teno virus

<400> SEQUENCE: 73

```
aguccagugc acuacuccua c                                              21
```

<210> SEQ ID NO 74
<211> LENGTH: 31
<212> TYPE: RNA
<213> ORGANISM: homo sapiens

<400> SEQUENCE: 74

```
uggcaccugc uguuucuaaa acagaggaug u                                   31
```

<210> SEQ ID NO 75
<211> LENGTH: 20
<212> TYPE: RNA
<213> ORGANISM: torque teno virus

<400> SEQUENCE: 75

```
guccagugca cuacuccuac                                                20
```

<210> SEQ ID NO 76
<211> LENGTH: 33
<212> TYPE: RNA
<213> ORGANISM: homo sapiens

<400> SEQUENCE: 76

```
aguucucuag auuuugauga ugaugauguu gac                                 33
```

<210> SEQ ID NO 77
<211> LENGTH: 22
<212> TYPE: RNA
<213> ORGANISM: torque teno virus

<400> SEQUENCE: 77

```
caggaggggu gcacugcaac ug                                             22
```

<210> SEQ ID NO 78
<211> LENGTH: 10848
<212> TYPE: DNA
<213> ORGANISM: homo sapiens

<400> SEQUENCE: 78

```
gtattggtgc agcccgccag ggtgtcactg gagacagaat ggaggtgctg ccggactcgg    60
aaatggggac acatgcattg gtggccaaaa gagagaggag acaaaaccgc tgcagatggc   120
tgatgtgaat ctagtggaaa gagctactgg ggatgagaga agaggagga ggcaggtcca    180
agggtagcca aggatggctg cagcttcata tgatcagttg ttaaagcaag ttgaggcact   240
gaagatggag aactcaaatc ttcgacaaga gctagaagat aattccaatc atcttacaaa   300
actgaaaact gaggcatcta atatgaagga agtacttaaa caactacaag gaagtattga   360
agatgaagct atggcttctt ctggacagat tgatttatta gagcgtctta aagagcttaa   420
cttagatagc agtaatttcc ctggagtaaa actgcggtca aaaatgtccc tccgttctta   480
tggaagccgg gaaggatctg tatcaagccg ttctggagag tgcagtcctg ttcctatggg   540
```

```
ttcatttcca agaagagggt tgtaaatgg aagcagagaa agtactggat atttagaaga    600
acttgagaaa gagaggtcat tgcttcttgc tgatcttgac aaagaagaaa aggaaaaaga    660
ctggtattac gctcaacttc agaatctcac taaaagaata gatagtcttc ctttaactga    720
aaatttttcc ttacaaacag atatgaccag aaggcaattg gaatatgaag caaggcaaat    780
cagagttgcg atggaagaac aactaggtac ctgccaggat atggaaaaac gagcacagcg    840
aagaatagcc agaattcagc aaatcgaaaa ggacatactt cgtatacgac agcttttaca    900
gtcccaagca acagaagcag agaggtcatc tcagaacaag catgaaaccg gctcacatga    960
tgctgagcgg cagaatgaag gtcaaggagt gggagaaatc aacatggcaa cttctggtaa   1020
tggtcagggt tcaactacac gaatggacca tgaaacagcc agtgttttga gttctagtag   1080
cacacactct gcacctcgaa ggctgacaag tcatctggga accaaggtgg aaatggtgta   1140
ttcattgttg tcaatgcttg gtactcatga taaggatgat atgtcgcgaa cttttgctagc  1200 tatgtctagc tcccaagaca gctgtatatc catgcgacag tctggatgtc ttcctctcct   1260
catccagctt ttacatggca atgacaaaga ctctgtattg ttgggaaatt cccggggcag   1320
taaagaggct cgggccaggg ccagtgcagc actccacaac atcattcact cacagcctga   1380
tgacaagaga ggcaggcgtg aaatccgagt ccttcatctt ttggaacaga tacgcgctta   1440
ctgtgaaacc tgttgggagt ggcaggaagc tcatgaacca ggcatggacc aggacaaaaa   1500
tccaatgcca gctcctgttg aacatcagat ctgtcctgct gtgtgtgttc taatgaaact   1560
ttcatttgat gaagagcata gacatgcaat gaatgaacta ggggactac aggccattgc    1620 agaattattg caagtggact gtgaaatgta tgggcttact aatgaccact acagtattac   1680
actaagacga tatgctggaa tggctttgac aaacttgact tttggagatg tagccaacaa   1740
ggctacgcta tgctctatga aaggctgcat gagagcactt gtggcccaac taaaatctga   1800
aagtgaagac ttacagcagg ttattgcgag tgttttgagg aatttgtctt ggcgagcaga   1860
tgtaaatagt aaaaagacgt tgcgagaagt tggaagtgtg aaagcattga tggaatgtgc   1920
tttagaagtt aaaaaggaat caaccctcaa aagcgtattg agtgccttat ggaatttgtc   1980
agcacattgc actgagaata agctgatat atgtgctgta gatggtgcac ttgcattttt   2040
ggttggcact cttacttacc ggagccagac aaacacttta gccattattg aaagtggagg   2100
tgggatatta cggaatgtgt ccagcttgat agctacaaat gaggaccaca ggcaaatcct   2160
aagagagaac aactgtctac aaactttatt acaacactta aaatctcata gtttgacaat   2220
agtcagtaat gcatgtggaa cttttgtggaa tctctcagca agaaatccta agaccagga    2280 agcattatgg gacatggggg cagttagcat gctcaagaac ctcattcatt caaagcacaa   2340
aatgattgct atgggaagtg ctgcagcttt aaggaatctc atggcaaata ggcctgcgaa   2400
gtacaaggat gccaatatta tgtctcctgg ctcaagcttg ccatctcttc atgttaggaa   2460
acaaaaagcc ctagaagcag aattagatgc tcagcactta tcagaaactt ttgacaatat   2520
agacaattta agtcccaagg catctcatcg tagtaagcag agacacaagc aaagtctcta   2580
tggtgattat gttttgaca ccaatcgaca tgatgataat aggtcagaca attttaatac    2640
tggcaacatg actgtccttt caccatattt gaatactaca gtgttaccca gctcctcttc   2700
atcaagagga agcttagata gttctcgttc tgaaaaagat agaagtttgg agagagaacg   2760
cggaattggt ctaggcaact accatccagc aacagaaaat ccaggaactt cttcaaagcg   2820
aggtttgcag atctccacca ctgcagccca gattgccaaa gtcatggaag aagtgtcagc   2880
cattcatacc tctcaggaag acagaagttc tgggtctacc actgaattac attgtgtgac   2940
```

```
agatgagaga aatgcactta gaagaagctc tgctgcccat acacattcaa acacttacaa   3000
tttcactaag tcggaaaatt caaataggac atgttctatg ccttatgcca aattagaata   3060
caagagatct tcaaatgata gtttaaatag tgtcagtagt agtgatggtt atggtaaaag   3120
aggtcaaatg aaaccctcga ttgaatccta ttctgaagat gatgaaagta agttttgcag   3180
ttatggtcaa tacccagccg acctagccca taaaatacat agtgcaaatc atatggatga   3240
taatgatgga gaactagata caccaataaa ttatagtctt aaatattcag atgagcagtt   3300
gaactctgga aggcaaagtc cttcacagaa tgaaagatgg gcaagaccca aacacataat   3360
agaagatgaa ataaaacaaa gtgagcaaag acaatcaagg aatcaaagta caacttatcc   3420
tgtttatact gagagcactg atgataaaca cctcaagttc caaccacatt ttggacagca   3480
ggaatgtgtt tctccataca ggtcacgggg agccaatggt tcagaaacaa atcgagtggg   3540
ttctaatcat ggaattaatc aaaatgtaag ccagtctttg tgtcaagaag atgactatga   3600
agatgataag cctaccaatt atagtgaacg ttactctgaa gaagaacagc atgaagaaga   3660
agagagacca acaaattata gcataaaata taatgaagag aaacgtcatg tggatcagcc   3720
tattgattat agtttaaaat atgccacaga tattccttca tcacagaaac agtcattttc   3780
attctcaaag agttcatctg acaaagcag taaaaccgaa catatgtctt caagcagtga   3840 gaatcgtcc acaccttcat ctaatgccaa gaggcagaat cagctccatc caagttctgc   3900
acagagtaga agtggtcagc ctcaaaaggc tgccacttgc aaagtttctt ctattaacca   3960
agaaacaata cagacttatt gtgtagaaga tactccaata tgttttttcaa gatgtagttc   4020 attatcatct ttgtcatcag ctgaagatga aataggatgt aatcagacga cacaggaagc   4080
agattctgct aatacccctgc aaatagcaga aataaaagaa aagattggaa ctaggtcagc   4140
tgaagatcct gtgagcgaag ttccagcagt gtcacagcac cctagaacca aatccagcag   4200
actgcagggt tctagtttat cttcagaatc agccaggcac aaagctgttg aattttcttc   4260
aggagcgaaa tctccctcca aaagtggtgc tcagacaccc aaaagtccac ctgaacacta   4320
tgttcaggag accccactca tgtttagcag atgtacttct gtcagttcac ttgatagttt   4380
tgagagtcgt tcgattgcca gctccgttca gagtgaacca tgcagtggaa tggtaagtgg   4440
cattataagc cccagtgatc ttccagatag ccctggacaa accatgccac caagcagaag   4500
taaaacacct ccaccacctc ctcaaacagc tcaaaccaag cgagaagtac ctaaaaataa   4560
agcacctact gctgaaaaga gagagagtgg acctaagcaa gctgcagtaa atgctgcagt   4620
tcagagggtc caggttcttc cagatgctga tactttatta cattttgcca cggaaagtac   4680
tccagatgga ttttcttgtt catccagcct gagtgctctg agcctcgatg agccatttat   4740
acagaaagat gtgaattaa gaataatgcc tccagttcag gaaatgaca atgggaatga   4800 aacagaatca gagcagccta agaatcaaa tgaaaccaa gagaaagagg cagaaaaaac   4860
tattgattct gaaaaggacc tattagtga ttcagatgat gatgatattg aaatactaga   4920
agaatgtatt atttctgcca tgccaacaaa gtcatcacgt aaagcaaaaa agccagccca   4980
gactgcttca aaattacctc cacctgtggc aaggaaacca agtcagctgc ctgtgtacaa   5040
acttctacca tcacaaaaca ggttgcaacc ccaaaagcat gttagttta caccggggga   5100 tgatatgcca cgggtgtatt gtgttgaagg gacacctata aacttttcca cagctacatc   5160
tctaagtgat ctaacaatcg aatcccctcc aaatgagtta gctgctggag aaggagttag   5220
aggaggggca cagtcaggtg aatttgaaaa acagagatacc attcctacag aaggcagaag   5280
```

```
tacagatgag gctcaaggag gaaaaacctc atctgtaacc atacctgaat tggatgacaa      5340
taaagcagag gaaggtgata ttcttgcaga atgcattaat tctgctatgc ccaaagggaa      5400
aagtcacaag cctttccgtg tgaaaaagat aatggaccag gtccagcaag catctgcgtc      5460
ttcttctgca cccaacaaaa atcagttaga tggtaagaaa aagaaaccaa cttcaccagt      5520
aaaacctata ccacaaaata ctgaatatag gacacgtgta agaaaaatg cagactcaaa       5580 aaataattta aatgctgaga gagttttctc agacaacaaa gattcaaaga aacagaattt      5640 gaaaataat tccaaggtct tcaatgataa gctcccaaat aatgaagata gagtcagagg       5700
aagttttgct tttgattcac ctcatcatta acgcctatt gaaggaactc cttactgttt       5760
ttcacgaaat gattctttga gttctctaga ttttgatgat gatgatgttg accttttccag     5820 ggaaaaggct gaattaagaa aggcaaaaga aaataaggaa tcagaggcta aagttaccag      5880
ccacacagaa ctaacctcca accaacaatc agctaataag acacaagcta ttgcaaagca      5940
gccaataaat cgaggtcagc ctaaacccat acttcagaaa caatccactt ttccccagtc      6000
atccaaagac ataccagaca gagggcagc aactgatgaa aagttacaga attttgctat       6060
tgaaaatact ccggttctgct tttctcataa ttcctctctg agttctctca gtgacattga     6120
ccaagaaaac aacaataaag aaaatgaacc tatcaaagag actgagcccc ctgactcaca      6180
gggagaacca agtaaacctc aagcatcagg ctatgctcct aaatcatttc atgttgaaga      6240
taccccagtt tgtttctcaa gaaacagttc tctcagttct cttagtattg actctgaaga      6300
tgacctgttg caggaatgta taagctccgc aatgccaaaa aagaaaaagc cttcaagact      6360
caagggtgat aatgaaaaac atagtcccag aaatatgggt ggcatattag gtgaagatct      6420
gacacttgat ttgaaagata tacagagacc agattcagaa catggtctat cccctgattc      6480
agaaaatttt gattggaaag ctattcagga aggtgcaaat tccatagtaa gtagtttaca      6540
tcaagctgct gctgctgcat gtttatctag acaagcttcg tctgattcag attccatcct      6600
ttccctgaaa tcaggaatct ctctgggatc accatttcat cttacacctg atcaagaaga      6660
aaaacccttt acaagtaata aaggcccacg aattctaaaa ccaggggaga aaagtacatt      6720
ggaaactaaa aagatagaat ctgaaagtaa aggaatcaaa ggaggaaaaa aagttttataa     6780 aagtttgatt actggaaaag ttcgatctaa ttcagaaatt tcaggccaaa tgaaacagcc      6840
ccttcaagca aacatgcctt caatctctcg aggcaggaca atgattcata ttccaggagt      6900
tcgaaatagc tcctcaagta caagtcctgt ttctaaaaaa ggcccacccc ttaagactcc      6960
agcctccaaa agccctagtg aaggtcaaac agccaccact tctcctagag gagccaagcc      7020
atctgtgaaa tcagaattaa gccctgttgc caggcagaca tcccaaatag gtgggtcaag      7080
taaagcacct tctagatcag gatctagaga ttcgacccct tcaagacctg cccagcaacc      7140
attaagtaga cctatacagt ctcctggccg aaactcaatt tcccctggta gaaatggaat      7200
aagtcctcct aacaaattat ctcaacttcc aaggacatca tccccctagta ctgcttcaac     7260 taagtcctca ggttctggaa aaatgtcata tacatctcca ggtagacaga tgagccaaca      7320
gaaccttacc aaacaaacag gtttatccaa gaatgccagt agtattccaa gaagtgagtc      7380
tgcctccaaa ggactaaatc agatgaataa tggtaatgga gccaataaaa aggtagaact      7440
ttctagaatg tcttcaacta atcaagtgg aagtgaatct gatagatcag aaagacctgt       7500
attagtacgc cagtcaactt tcatcaaaga agctccaagc ccaaccttaa gaagaaaatt      7560
ggaggaatct gcttcatttg aatctctttc tccatcatct agaccagctt ctcccactag      7620
gtcccaggca caaactccag ttttaagtcc ttcccttcct gatatgtctc tatccacaca      7680
```

```
ttcgtctgtt caggctggtg gatggcgaaa actcccacct aatctcagtc ccactataga    7740
gtataatgat ggaagaccag caaagcgcca tgatattgca cggtctcatt ctgaaagtcc    7800
ttctagactt ccaatcaata ggtcaggaac ctggaaacgt gagcacagca aacattcatc    7860
atcccttcct cgagtaagca cttggagaag aactggaagt tcatcttcaa ttctttctgc    7920
ttcatcagaa tccagtgaaa aagcaaaaag tgaggatgaa aaacatgtga actctatttc    7980
aggaaccaaa caaagtaaag aaaaccaagt atccgcaaaa ggaacatgga gaaaaataaa    8040
agaaaatgaa ttttctccca caaatagtac ttctcagacc gtttcctcag gtgctacaaa    8100
tggtgctgaa tcaaagactc taatttatca aatggcacct gctgtttcta aaacagagga    8160
tgtttgggtg agaattgagg actgtcccat taacaatcct agatctggaa gatctcccac    8220
aggtaatact cccccggtga ttgacagtgt ttcagaaaag gcaaatccaa acattaaaga    8280
ttcaaaagat aatcaggcaa acaaaatgt gggtaatggc agtgttccca tgcgtaccgt    8340
gggtttggaa aatcgcctga actccttat tcaggtggat gcccctgacc aaaaaggaac    8400
tgagataaaa ccaggacaaa ataatcctgt ccctgtatca gagactaatg aaagttctat    8460
agtggaacgt accccattca gttctagcag ctcaagcaaa cacagttcac ctagtgggac    8520
tgttgctgcc agagtgactc ctttaatta caacccaagc cctaggaaaa gcagcgcaga    8580
tagcacttca gctcggccat ctcagatccc aactccagtg aataacaaca caagaagcg    8640
agattccaaa actgacagca cagaatccag tggaacccaa agtcctaagc gccattctgg    8700
gtcttacctt gtgacatctg tttaaaagag aggaagaatg aaactaagaa aattctatgt    8760
taattacaac tgctatatag acattttgtt tcaaatgaaa ctttaaaaga ctgaaaaatt    8820
ttgtaaatag gtttgattct tgttagaggg tttttgttct ggaagccata tttgatagta    8880
tactttgtct tcactggtct tattttggga ggcactcttg atggttagga aaaaaatagt    8940
aaagccaagt atgtttgtac agtatgtttt acatgtattt aaagtagcat cccatcccaa    9000
cttcctttaa ttattgcttg tcttaaaata atgaacacta cagatagaaa atatgatata    9060
ttgctgttat caatcattc tagattataa actgactaaa cttacatcag ggaaaaattg    9120
gtatttatgc aaaaaaaaat gttttgtcc ttgtgagtcc atctaacatc ataattaatc    9180
atgtggctgt gaaattcaca gtaatatggt tcccgatgaa caagtttacc cagcctgctt    9240
tgctttactg catgaatgaa actgatggtt caatttcaga agtaatgatt aacagttatg    9300
tggtcacatg atgtgcatag agatagctac agtgtaataa tttacactat tttgtgctcc    9360
aaacaaaaca aaaatctgtg taactgtaaa acattgaatg aaactatttt acctgaacta    9420
gattttatct gaaagtaggt agaattttg ctatgctgta atttgttgta tattctggta    9480
tttgaggtga gatggctgct cttttattaa tgagacatga attgtgtctc aacagaaact    9540
aaatgaacat ttcagaataa attattgctg tatgtaaact gttactgaaa ttggtatttg    9600
tttgaagggt cttgtttcac atttgtatta ataattgttt aaaatgcctc ttttaaaagc    9660
ttatataaat ttttttcttc agcttctatg cattaagagt aaaattcctc ttactgtaat    9720
aaaaacaatt gaagaagact gttgccactt aaccattcca tgcgttggca cttatctatt    9780
cctgaaattt ctttatgtg attagctcat cttgattttt aatattttc cacttaaact    9840
ttttttttctt actccactgg agctcagtaa aagtaaattc atgtaatagc aatgcaagca    9900
gcctagcaca gactaagcat tgagcataat aggcccacat aatttcctct tcttaatat    9960
tatagaattc tgtacttgaa attgattctt agacattgca gtctcttcga ggctttacag   10020
```

```
tgtaaactgt cttgcccctt catcttcttg ttgcaactgg gtctgacatg aacactttt      10080 atcaccctgt atgttagggc aagatctcag cagtgaagta taatcagcac tttgccatgc      10140
tcagaaaatt caaatcacat ggaactttag aggtagattt aatacgatta agatattcag      10200
aagtatattt tagaatccct gcctgttaag gaaactttat ttgtggtagg tacagttctg      10260
gggtacatgt taagtgtccc cttatacagt ggagggaagt cttccttcct gaaggaaaat      10320
aaactgacac ttattaacta agataattta cttaatatat cttccctgat ttgttttaaa      10380
agatcagagg gtgactgatg atacatgcat acatatttgt tgaataaatg aaaatttatt      10440
tttagtgata agattcatac actctgtatt tggggaggga aaacctttt aagcatggtg       10500 gggcactcag ataggagtga atacacctac ctggtgcctt gaaaatcaca tcaagtagtt      10560
aattatctac cccttacctg tgtttataac ttccaggtaa tgagaatgat ttttttaaa       10620 gctaaaatgc cagtaaataa aagtgctatg acttgagcta agatatttga ctccaatgcc      10680
tgtactgtgt ctactgcacc actttgtaaa cacttcaatt tactatcttt gaatgattg       10740 acctttaaat ttttgccaaa tgttatctga aattgtctat gaataccatc tacttctgtt      10800
gttttcccag gcttccataa acaatggaga tacatgcaaa aaaaaaaa                   10848
```

<210> SEQ ID NO 79
<211> LENGTH: 33
<212> TYPE: DNA
<213> ORGANISM: artificial sequence
<220> FEATURE:
<223> OTHER INFORMATION: primer TT-ON9

<400> SEQUENCE: 79
gattatggta cctttccaac tacgactggg tgt                                    33

<210> SEQ ID NO 80
<211> LENGTH: 34
<212> TYPE: DNA
<213> ORGANISM: artificial sequence
<220> FEATURE:
<223> OTHER INFORMATION: primer TT-ON10

<400> SEQUENCE: 80
gattatggta cctctaccat tcgtcaccgc tgtt                                   34

<210> SEQ ID NO 81
<211> LENGTH: 18
<212> TYPE: RNA
<213> ORGANISM: homo sapiens

<400> SEQUENCE: 81
accauuccau gcguuggc                                                     18

<210> SEQ ID NO 82
<211> LENGTH: 22
<212> TYPE: RNA
<213> ORGANISM: torque teno virus

<400> SEQUENCE: 82
caggaggggu gcacugcaac ug                                                22

<210> SEQ ID NO 83
<211> LENGTH: 23
<212> TYPE: RNA
<213> ORGANISM: homo sapiens

<400> SEQUENCE: 83

-continued

```
cuccuaaauc auuucauguu gaa                                    23

<210> SEQ ID NO 84
<211> LENGTH: 21
<212> TYPE: RNA
<213> ORGANISM: torque teno virus

<400> SEQUENCE: 84
caggaggggu gcacugcaac u                                      21

<210> SEQ ID NO 85
<211> LENGTH: 45
<212> TYPE: RNA
<213> ORGANISM: homo sapiens

<400> SEQUENCE: 85
acagguugca accccaaaag cauguuaguu uuacaccggg ggaug            45

<210> SEQ ID NO 86
<211> LENGTH: 21
<212> TYPE: RNA
<213> ORGANISM: torque teno virus

<400> SEQUENCE: 86
aguccagugc acuacccua c                                       21

<210> SEQ ID NO 87
<211> LENGTH: 33
<212> TYPE: RNA
<213> ORGANISM: homo sapiens

<400> SEQUENCE: 87
ccgccggaag ccuagccgcu gcucgggggg gac                         33

<210> SEQ ID NO 88
<211> LENGTH: 24
<212> TYPE: RNA
<213> ORGANISM: torque teno virus

<400> SEQUENCE: 88
ugcaguugca gugcaccccu ccug                                   24

<210> SEQ ID NO 89
<211> LENGTH: 44
<212> TYPE: RNA
<213> ORGANISM: homo sapiens

<400> SEQUENCE: 89
ugcgcauugu agucuuccca ccucccacaa gauggcggag ggca             44

<210> SEQ ID NO 90
<211> LENGTH: 24
<212> TYPE: RNA
<213> ORGANISM: torque teno virus

<400> SEQUENCE: 90
ugcaguugca gugcaccccu ccug                                   24

<210> SEQ ID NO 91
<211> LENGTH: 30
<212> TYPE: RNA
<213> ORGANISM: homo sapiens
```

```
<400> SEQUENCE: 91
ccauggcgag gcuugcugcg gggggagggg                    30

<210> SEQ ID NO 92
<211> LENGTH: 24
<212> TYPE: RNA
<213> ORGANISM: torque teno virus

<400> SEQUENCE: 92
ugcaguugca gugcacccCu ccug                          24

<210> SEQ ID NO 93
<211> LENGTH: 25
<212> TYPE: RNA
<213> ORGANISM: homo sapiens

<400> SEQUENCE: 93 uuguuuuuu uuuggcgggg ggggu                          25

<210> SEQ ID NO 94
<211> LENGTH: 24
<212> TYPE: RNA
<213> ORGANISM: torque teno virus

<400> SEQUENCE: 94
ugcaguugca gugcacccCu ccug                          24
```